(12) United States Patent
Mohammad M. B. B. S.

(10) Patent No.: US 6,379,337 B1
(45) Date of Patent: Apr. 30, 2002

(54) RETRACTABLE SAFETY NEEDLES FOR MEDICAL APPLICATIONS

(76) Inventor: Owais Mohammad M. B. B. S., 5004 Rittenhouse St., Riverdale, MD (US) 20737

( * ) Notice: Subject to any disclaimer, the term of this patent is extended or adjusted under 35 U.S.C. 154(b) by 0 days.

(21) Appl. No.: 09/471,094

(22) Filed: Dec. 23, 1999

Related U.S. Application Data

(63) Continuation-in-part of application No. 09/218,040, filed on Dec. 22, 1998, now Pat. No. 6,162,197.

(51) Int. Cl.[7] .................................................. A61M 5/32
(52) U.S. Cl. ........................ 604/195; 604/263; 604/162; 604/163
(58) Field of Search ................................ 604/263, 264, 604/272, 187, 162, 163, 195; 606/167, 185, 187

(56) References Cited

U.S. PATENT DOCUMENTS

| 3,134,380 A | * | 5/1964 | Armao | 604/198 |
| 3,892,237 A | * | 7/1975 | Steiner | 128/216 |
| 4,416,663 A | | 11/1983 | Hall | 604/163 |
| 4,425,120 A | | 1/1984 | Sampson | 604/198 |
| 4,564,054 A | | 1/1986 | Gustavsson | 141/329 |
| 4,639,249 A | | 1/1987 | Larson | 604/198 |
| 4,664,654 A | | 5/1987 | Strauss | 604/198 |
| 4,725,267 A | | 2/1988 | Vaillancourt | 604/198 |
| 4,735,618 A | | 4/1988 | Hagen | 604/192 |
| 4,737,150 A | | 4/1988 | Baeumle et al. | 604/198 |
| 4,758,231 A | | 7/1988 | Haber et al. | 604/198 |
| 4,772,272 A | | 9/1988 | McFarland | 604/192 |
| 4,795,432 A | | 1/1989 | Karczmer | 604/110 |
| 4,804,371 A | | 2/1989 | Vaillancourt | 604/198 |
| 4,816,022 A | | 3/1989 | Poncy | 604/198 |
| 4,838,863 A | | 6/1989 | Allard et al. | 604/110 |
| 4,842,587 A | | 6/1989 | Poncy | 604/198 |
| 4,846,809 A | | 7/1989 | Sims | 604/198 |
| 4,863,436 A | | 9/1989 | Glick | 604/198 |
| 4,887,998 A | | 12/1989 | Martin et al. | 604/110 |
| 4,900,307 A | | 2/1990 | Kulli | 604/110 |
| 4,900,311 A | | 2/1990 | Stern et al. | 604/198 |
| 4,915,697 A | | 4/1990 | DuPont | 604/192 |
| 4,917,669 A | * | 4/1990 | Bonaldo | 604/164 |
| 4,917,673 A | | 4/1990 | Coplin | 604/198 |
| 4,923,445 A | | 5/1990 | Ryan | 604/195 |
| 4,927,416 A | | 5/1990 | Tomkiel | 604/198 |
| 4,929,237 A | | 5/1990 | Medway | 604/198 |
| 4,943,282 A | | 7/1990 | Page et al. | 604/198 |
| 4,966,592 A | | 10/1990 | Burns et al. | 604/198 |

(List continued on next page.)

Primary Examiner—Glenn K. Dawson
Assistant Examiner—Jennifer Maynard
(74) Attorney, Agent, or Firm—Kramer & Associates

(57) ABSTRACT

A retractable needle for use with a catheter, featuring a cylindrical hub having a hollow needle extending through the hub. The hub has a flash chamber connected thereto where the interior of the needle is in fluid communication with the interior of the flash chamber. The hub is slidably positioned in a housing having a wall with a longitudinal slot therein. A stem connected with the hub passes through the slot, and has a thumbrest rigidly fixed thereto, where the thumbrest may be used to manually move the knob from a first locking position, where the needle is retracted within the housing, to a second locking position where the needle is exposed. A catheter is mounted on the needle when the needle is exposed. Also disclosed are blood-drawing needles comprising a cylindrical hub having a hollow needle extending from one end of the hub. The hub has a cavity adapted to frictionally engage the tip of a syringe barrel on its other end. The hub is slidably positioned in a housing having a wall with a longitudinal slot therein. A stem connected with the hub passes through the slot, and has a thumbrest rigidly fixed thereto, where the thumbrest may be used to manually move the knob from a first locking position, where the needle is retracted within the housing, to a second locking position where the needle is exposed.

42 Claims, 11 Drawing Sheets

U.S. PATENT DOCUMENTS

| | | | |
|---|---|---|---|
| 4,998,924 A | | 3/1991 | Ranford ............. 604/798 |
| 5,000,740 A | * | 3/1991 | Ducharme et al. ........ 604/162 |
| 5,011,475 A | | 4/1991 | Olson .............. 604/192 |
| RE33,585 E | | 5/1991 | Haber et al. ........... 604/198 |
| 5,013,304 A | * | 5/1991 | Russell et al. ........... 604/167 |
| 5,086,780 A | | 2/1992 | Schmitt ............ 604/194 |
| 5,088,986 A | | 2/1992 | Nusbaum ........... 604/198 |
| 5,092,845 A | | 3/1992 | Chang ............. 604/164 |
| 5,104,385 A | | 4/1992 | Huband ............ 604/198 |
| 5,106,379 A | | 4/1992 | Leap .............. 604/198 |
| 5,125,414 A | | 6/1992 | Dysarz ............. 128/763 |
| RE34,045 E | | 8/1992 | McFarland .......... 604/198 |
| 5,219,338 A | | 6/1993 | Haworth ............ 664/198 |
| 5,222,947 A | | 6/1993 | D'Amico ........... 604/198 |
| 5,232,456 A | | 8/1993 | Gonzalez ........... 604/192 |
| 5,246,428 A | | 9/1993 | Falknor ............ 604/198 |
| 5,254,100 A | | 10/1993 | Huband ............ 604/198 |
| 5,279,579 A | | 1/1994 | D'Amico ........... 604/192 |
| 5,279,590 A | * | 1/1994 | Sinko et al. ......... 604/263 |
| 5,290,255 A | | 3/1994 | Vallelunga et al. ...... 604/197 |
| 5,312,359 A | * | 5/1994 | Wallace et al. ........ 604/164 |
| 5,411,487 A | | 5/1995 | Castagna ........... 604/198 |
| 5,423,758 A | | 6/1995 | Shaw .............. 604/195 |
| 5,501,675 A | * | 3/1996 | Erskine ............ 604/263 |
| 5,573,513 A | | 11/1996 | Wozencroft .......... 604/198 |
| 5,591,138 A | | 1/1997 | Vaillancourt ......... 604/263 |
| 5,685,855 A | * | 11/1997 | Erskine ............ 604/108 |
| 5,695,474 A | * | 12/1997 | Daugherty .......... 604/162 |
| 5,695,475 A | | 12/1997 | Best, Jr. et al. ......... 604/198 |
| 5,769,826 A | | 6/1998 | Johnson et al. ........ 604/195 |
| 5,779,679 A | * | 7/1998 | Shaw .............. 604/158 |
| 5,788,677 A | | 8/1998 | Botich et al. ......... 604/195 |
| 5,824,001 A | * | 10/1998 | Erskine ............ 604/158 |
| 5,830,190 A | * | 11/1998 | Howell ............ 604/168 |

\* cited by examiner

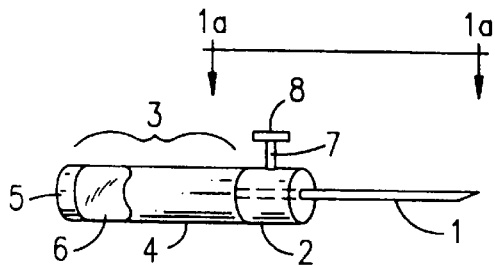
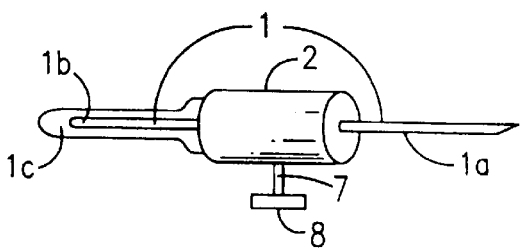
FIG.1          FIG.2
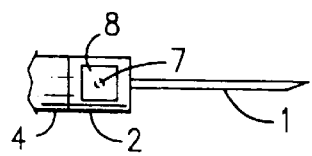
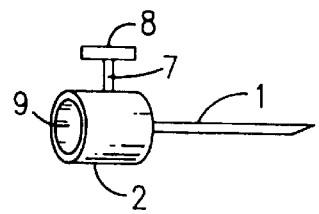
FIG.1a         FIG.3
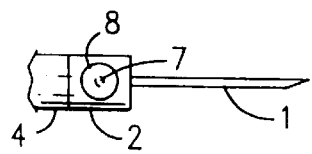
FIG.1b
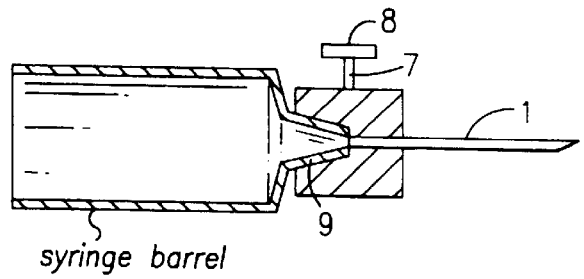
FIG.4
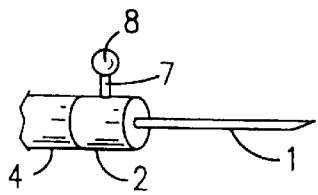
FIG.1c
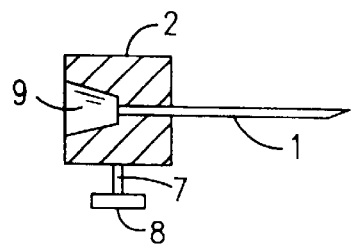
FIG.5a
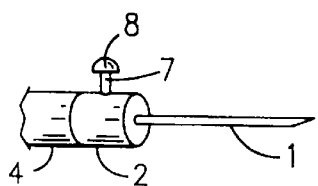
FIG.1d
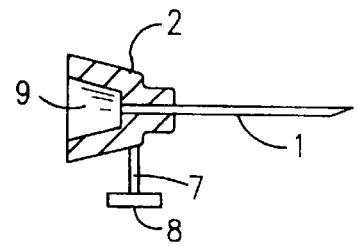
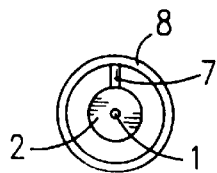
FIG.1e         FIG.5b

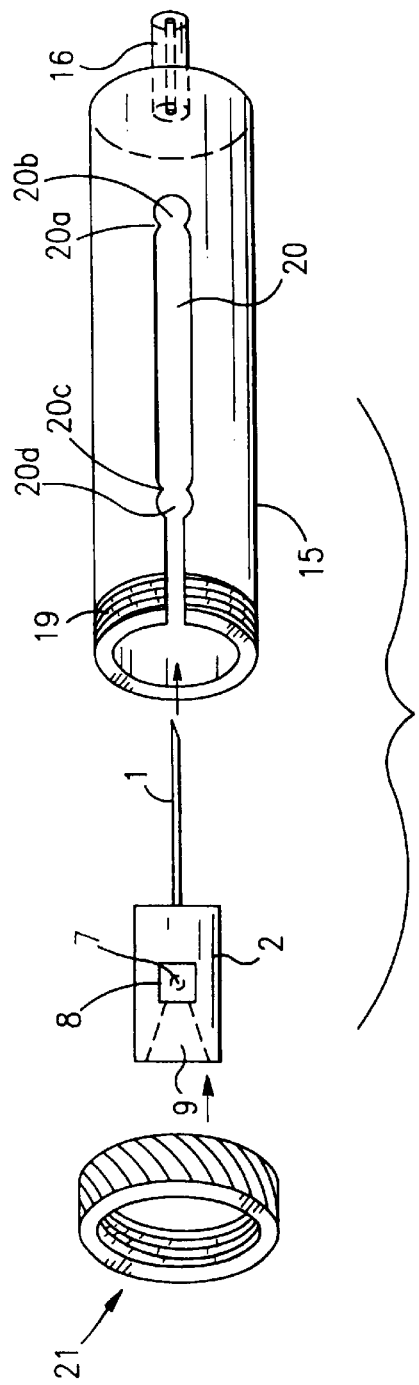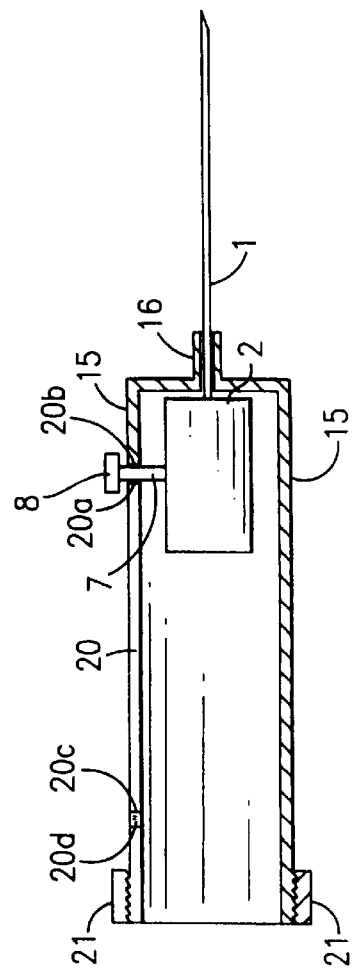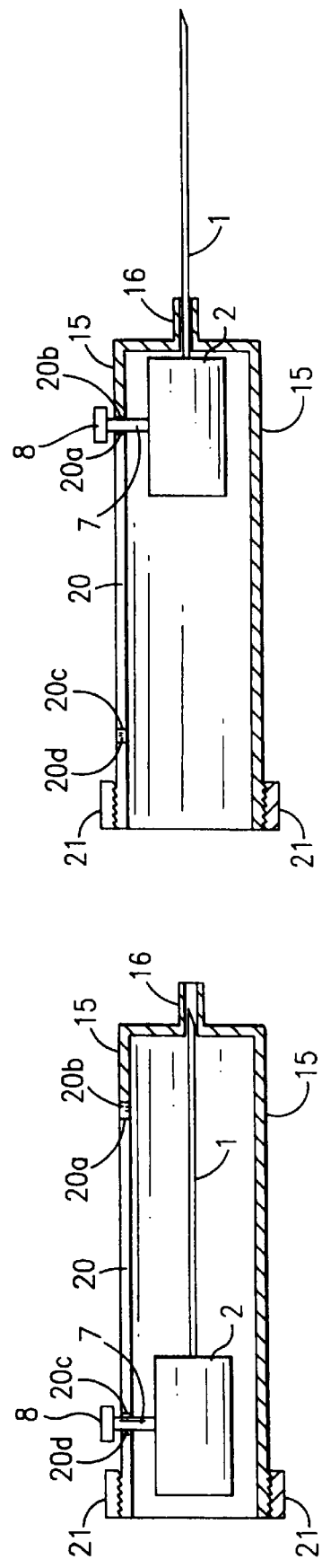
FIG. 12
FIG. 13a
FIG. 13b

RETRACTABLE SAFETY NEEDLES FOR MEDICAL APPLICATIONS

This application is a continuation-in-part of U.S. patent application Ser. No. 09/218,040, filed Dec. 22, 1998, now U.S. Pat. No. 6,162,197.

BACKGROUND OF THE INVENTION

The present invention generally refers to retractable needles for use in insertion of a catheter. Additionally, the invention relates to hypodermic syringe needles for medical use. More particularly, the invention relates to hypodermic safety needles which retract into a container when not in use, preventing unintentional contact with the needle.

Prior art injection needles and catheter insertion needles feature hollow needles which extend through a plastic hub. To prevent a user from accidentally pricking himself with the point of a needle, the needle is covered with a removable cover. Such covers frictionally engage the plastic hub, and may be readily removed once the needle is attached to a syringe barrel. After use, the cover may be reattached to the needle assembly, which is then separated from the syringe barrel and discarded. However, there is an unacceptable risk of accidental injury resulting from contact with the point of the needle during the recapping step. This is particularly dangerous as biological fluids contaminating the needle could enter the user's bloodstream. An improved means of covering a used injection needle is needed.

A wide variety of needles having a means for shielding a syringe needle from accidental contact with a user's fingers have been developed. For example, U.S. Pat. No. 4,900,311, issued to Stem on Feb. 13, 1990, discloses a hypodermic syringe having a syringe barrel, an injection needle attached to the syringe barrel, and a needle guard of elliptical cross section disposed around the syringe barrel. The needle guard may be moved from a first position which covers the needle to a second position which exposes the needle. When the guard is in the second position, tabs on the interior of the guard engage slots on the syringe barrel, locking the guard into position. When the tabs are released from the slots by squeezing the elliptical guard along its longitudinal axis, a spring causes the guard to move into the first position, hiding the needle. The entire syringe assembly is then discarded.

This device, while useful, does have certain drawbacks. The syringe barrel used with this assembly has a highly specialized structure; a generic syringe barrel cannot readily be substituted. Also, the syringe barrel cannot readily be sterilized and reused. No provision for separation of the needle from the syringe barrel without removing the syringe needle from the protective needle guard is provided. Finally, there is the risk of accidentally squeezing the elliptical needle guard, causing the spring to move the needle guard into a position which conceals the needle prior to use of the needle.

U.S. Pat. No. 4,664,654, issued to Strauss on May 12, 1987, discloses a two piece needle shield comprising a sliding member and a stationary member. A latch holds the sliding member in position. When the latch is released, a spring causes the sliding member to retract inside the stationary member, exposing the needle. However, this device causes the user to place his hand in proximity to the needle at the time it is exposed, increasing the likelihood of injury from accidental contact with the needle.

U.S. Pat. No. 5,246,428, issued to Falknor on Sep. 21, 1993, discloses a needle safety mechanism comprising a base adapted to be fixed with respect to the needle, and a sheath which is movable between a first position which exposes the needle and a second position which covers the needle. A latch cooperative between the base and the sheath may be used to releasably latch the sheath in the position which covers the needle. A spring biases the sheath into the needle covering position. No mechanism for latching the sheath in a position which exposes the needle is provided, however. This may be an inconvenience for workers who wish to see the precise spot where they are administering an injection.

U.S. Pat. No. 5,279,579, issued to D'Amico on Jan. 18, 1994, discloses a self-capping injection needle assembly which includes a hub slidably positioned within a cylindrical cover adapted to receive a syringe barrel, and a needle mounted on the hub. A spring biases the hub into a position in which the needle is contained within the tubular cover. When the spring is compressed, the hub may slide into a position which exposes the needle. The hub includes a pin which slidably engages a longitudinal groove in the tubular cover. The groove includes a transverse leg adapted to receive the pin. When the pin is positioned in the transverse leg, the hub is releasably locked into a position which exposes the needle. The hub has a threaded female joint which may be screwed onto a syringe barrel having a corresponded threaded male joint. Different size tubular covers may be used for different size syringe barrels.

This device has certain disadvantages. First, in a medical environment time is often a critical factor. A more rapid method of affixing a needle to a syringe barrel than screwing it on is desirable. Also, only syringe barrels with a specific type of joint adapted to mate with the hub are usable with this device. Most commonly used medical syringe barrels have frusto-conical tips which frictionally engage syringe needle hubs having frusto-conical cavities therein; such commonly used barrels cannot be used with the threaded connections envisioned by D'Amico. D'Amico requires that a hub having a specific diameter must be used with a tubular cover having an inner diameter which is substantially equal to the hub diameter. Most commonly available syringe needle hubs have a single standard size, and cannot be used with a range of tubular cover sizes. Therefore, D'Amico's invention necessitates creation of a range of expensive and specialized syringe needles having a range of hub sizes. Also, since the diameter of D'Amico's hub is very nearly equal to the interior diameter of the tubular cover, it is difficult to insert a hub having a protruding pin into the cover. An easy method of assembling such a device is desirable.

U.S. Pat. No. 5,219,338, issued to Haworth on Jun. 15, 1993, and U.S. Pat. No. 5,695,474, issued to Daugherty on Dec. 9, 1997, disclose syringe assemblies in which one end of a retractable sheath is secured to a syringe barrel. The sheaths have circumferential accordion-like pleats which may be folded or unfolded. When the pleats are unfolded, the sheath is in an extended configuration, and covers a hypodermic needle secured to the syringe barrel. When the pleats are folded, the sheath is contracted so as to expose the needle. However, existing syringe barrels either cannot be used with this system, or they must be modified by securing a sheath to the exterior of the barrel before use with this system. Additionally, a wide variety of sheath sizes (one for each size syringe barrel) must be maintained in stock for such a retrofitting operation to be feasible.

U.S. Pat. No. 5,746,727, issued to Graves et al, discloses a safety needle assembly featuring a needle mounted to a hub having a radially projecting compressible knob, and a sheath having a longitudinal slot through which the knob projects. The hub is slidably mounted within the sheath. The slot extends from a first, which grips the knob so as to hold the hub in a position which exposes the needle, to a second locking position, which grips the knob so as to hold the hub in a position which conceals the needle within the sheath. Between the two locking positions, the slot is narrower than the diameter of the compressible knob. Thus, the device requires the application of significant force to move the knob along the slot between the locking positions, making the device awkward to use in situations where the needle must be manipulated rapidly, or handled with one hand.

Dufresne, in U.S. Pat. No. 5,817,065 and U.S. Pat. No. 5,607,402, discloses a safety needle holder having a double-ended needle mounted in a tubular housing. The needle passes through a hub having a pair of knobs which project radially from opposite sides of the hub. The knobs are each engaged by one of two longitudinal slots in the housing, where the longitudinal slots are on opposite sides of the housing. The slots are each of complicated structure, having three locking positions, each with a different shape, and a variety of different widths at different points along their length. The result is a complicated structure which is difficult to manufacture. It would be advantageous to have a housing structure having a slot of reduced complexity which is easier to manufacture.

There is a long-felt need in the art for a safety needle assembly which may be used for drawing blood, giving injections, or insertion of catheters, where the needle assembly has a retractable needle which may be easily assembled, and which may be used with commonly available syringe barrels having frusto-conical tips which frictionally engage a syringe needle assembly. The required safety needle assembly must also avoid the other disadvantages of known prior art devices. It is an object of this invention to provide such safety needle assemblies.

SUMMARY OF THE INVENTION

In a first embodiment, the invention is a retractable needle for use with a catheter. The needle features a cylindrical hub having an anterior end and a posterior end, with a hollow needle extending through the hub and projecting from the anterior end of the hub. The hub has a flash chamber connected thereto where the interior of the needle is in fluid communication with the interior of the flash chamber. The hub is slidably positioned in a tubular housing having a tubular wall with a longitudinal slot therein. A stem connected with the hub passes through the slot, and has a thumbrest rigidly fixed thereto, where the thumbrest is on the exterior of the housing and may be used to manually move the knob from a first locking position, where the needle is retracted within the housing, to a second locking position where the needle is exposed. A catheter is mounted on the needle when the needle assembly is exposed.

In a second embodiment, the invention is a retractable needle for use with a syringe. The needle features a cylindrical hub having an anterior end and a posterior end, with a hollow needle extending through the hub and projecting from the anterior end of the hub. The hub has a frusto-conical cavity adapted to frictionally engage the tip of a standard syringe. The hub is slidably positioned in a tubular housing having a tubular wall with a longitudinal slot therein. A stem connected with the hub passes through the slot, and has a thumbrest rigidly fixed thereto, where the thumbrest is on the exterior of the housing and may be used to manually move the knob from a first locking position, where the needle is retracted within the housing, to a second locking position where the needle is exposed.

In a third embodiment, the invention is a retractable needle for use in drawing blood. The needle features a cylindrical hub, with a hollow, double-ended needle extending therethrough. The hub is slidably positioned in a tubular housing having a tubular wall with a longitudinal slot therein. A stem connected with the hub passes through the slot, and has a thumbrest rigidly fixed thereto, where the thumbrest is on the exterior of the housing and may be used to manually move the knob from a first locking position, where the needle is retracted within the housing, to a second locking position where the needle is exposed.

In a fourth embodiment, the retractable needle of the invention features a adjustable-length tube having a first end and a second end. The adjustable-length tube has a length which may be reversibly altered from a first contracted length to a second extended length. A syringe barrel having a frustoconical tip may be secured to the first end of the adjustable-length tube, and a cylindrical hub having a hollow hypodermic needle attached thereto may be secured to the second end of the adjustable-length tube. The interior of the syringe barrel is in fluid contact with the interior of the a hollow hypodermic needle through the adjustable-length tube. A tubular sheath is disposed around the adjustable-length tube. The tubular sheath has a first end which is rigidly connected with the first end of the adjustable-length tube and a second end having an opening which is sufficiently large to allow the end of the hypodermic needle to pass therethrough. The length of the adjustable-length tube may be altered from the contracted length to the extended length. When the adjustable-length tube is contracted, the hypodermic needle is entirely disposed within the sheath. When the adjustable-length tube is extended, the end of the hypodermic needle is exposed through the opening in the second end of the sheath.

BRIEF DESCRIPTION OF THE DRAWINGS

FIGS. 1, 1*a*, 1*b*, 1*c*, 1*d*, and 1*e* illustrate various embodiments of a needle assembly for use with a catheter.

FIG. 2 illustrates a double-ended needle assembly for use in drawing blood.

FIGS. 3, 5*a*, and 5*b* illustrate needle assemblies for use with a hypodermic syringe.

FIG. 4 shows how a syringe engages a needle assembly of FIG. 3.

FIG. 12 illustrates assembly of a syringe needle having a retractable needle.

FIGS. 13*a* and 13*b* illustrate retractable syringes having their needles in different positions.

THE NEEDLE ASSEMBLY

Figure 6:
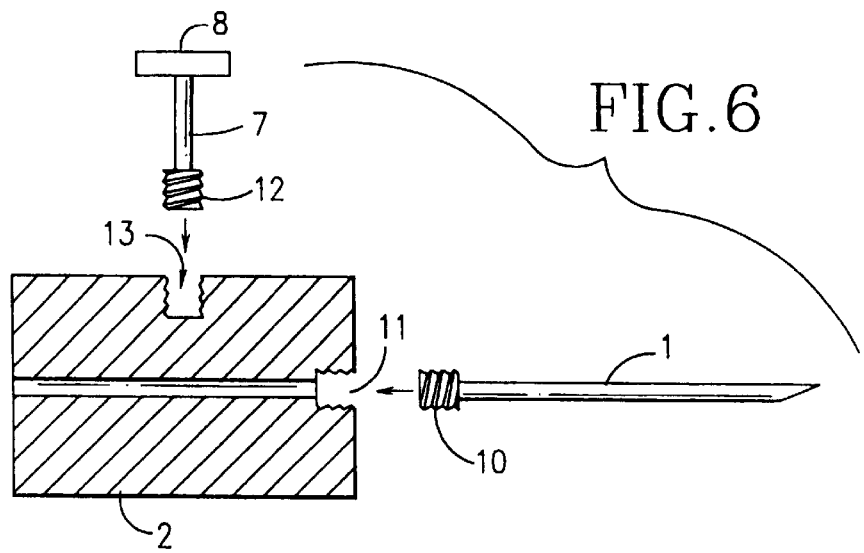
FIG. 6 illustrates assembly of a needle assembly.

The structure of the needle assembly depends in part upon its intended function, and will herein be described for each of the following purpose:

a) insertion of a catheter for delivery of fluids directly into the bloodstream of a patient;

b) withdrawal of a blood sample from a patient's blood vessel into an evacuated test tube; and c) transfer of fluids between a hypodermic syringe and the patient's blood vessel.

A needle assembly for use with a catheter is assembled as shown in FIG. 1. Hollow needle 1 extends from one end of a cylindrical hub 2, and penetrates the second end of the hub. A flash chamber 3 features a tubular side wall 4 having a first end which makes a watertight seal with the second end of hub 2. Cap 5 closes the second end of tubular wall 4, making a second leakproof seal. The interior of flash chamber 3 is in fluid communication with the interior of hollow needle 1, so that fluid may travel through the needle 1 into chamber 3. The tubular wall of chamber 3 is normally transparent or translucent, so that blood entering the flash chamber through needle 1 is readily visible. A small plug of cotton 6 is normally present in flash chamber 3, just under cap 5, although this is not an essential feature of the invention. A stem 7 protrudes radially from hub 2. A thumbrest 8 is attached to stem 7. The thumbrest may take any of several forms. It may be square, as shown in FIG. 1a. It may also be a round disk (FIG. 1b), a spherical knob (FIG. 1c), or a hemispherical knob (FIG. 1d). It may also take the form of a ring which encircles hub 2, without being connected to hub 2, except by means of stem 7 (FIG. 1e).

A needle assembly for use with an evacuated test tube is assembled as shown in FIG. 2. Hollow needle 1 extends through the axis of cylindrical hub 2. A first end 1a of the needle which is adapted to penetrate a patient's skin and enter a blood vessel extends from the first end of hub 2, and a second end 1b of the needle which is adapted to penetrate an elastomeric cap to an evacuated test tube extends from the second end of the hub. Needle end 1b is sealed in a leakproof manner by an elastomeric cover 1c. A stem 7 protrudes radially from hub 2. A thumbrest 8 is attached to stem 7. The thumbrest may take any of several forms, including those previously described for the catheter needle assembly. It may be a flat square, a round disk, a spherical knob, or a hemispherical knob. It may also take the form of a ring which encircles hub 2, without being connected to hub 2, except by means of stem 7.

A needle assembly for use with a hypodermic syringe is assembled as shown in FIG. 3. Hollow needle 1 extends through the axis of cylindrical hub 2. A first end 1a of the needle which is adapted to penetrate a patient's skin and enter a blood vessel extends from the first end of hub 2. A frusto-conical cavity 9 is present in the second end of hub 2. In this embodiment, the second end 1b of needle 1 terminates at a point which is flush with the bottom of cavity 9. Cavity 9 is adapted to receive the frusto-conical tip of a standard hypodermic syringe, as shown in FIG. 4. The external surface of hub 2 may be cylindrical, as shown in the cross-sectional view of FIG. 5a, or frusto-conical, as shown in the cross-sectional view of FIG. 5b. A stem 7 protrudes radially from hub 2. A thumbrest 8 is attached to stem 7. The thumbrest may take any of several forms, including those previously described for the catheter needle assembly. It may be a flat square, a round disk, a spherical knob, or a hemispherical knob. It may also take the form of a ring which encircles hub 2, without being connected to hub 2, except by means of stem 7.

In any of the above embodiments of the needle assembly, needle 1 may be secured to hub 2 by screwing a threaded male joint 10 provided on needle 1 into a threaded female joint 11 provided on the end of hub 2 (FIG. 6). Similarly, stem 7 may be secured to hub 2 by screwing a threaded male joint 12 provided on stem 7 into a threaded female joint 13 provided on the side of hub 2, provided that a ring-shaped thumbrest is not attached to the stem. If it is desired to use a ring-shaped thumbrest, stem 7 may be initially prepared with joint 12 on one end of stem 7 and no thumbrest on the other end of stem 7. Joint 12 may then be screwed into joint 13. Ring-shaped thumbrest 8 has a hole 14 directed radially through the ring which is adapted to receive the free end of stem 7. The hub may then be passed through the center of the ring-shaped thumbrest, until stem 7 may be inserted into hole 14 and adhesively secured to the thumbrest. However, the stem and the hub may also be manufactured as a single unit.

THE HOUSING

The housing for the needle assembly is manufactured in two parts (FIG. 7). The first part of the housing is a tubular sheath 15 having a defined outer diameter d1. Sheath 15 has a first end 16 having a hole 17 therethrough, where hole 17 is sufficiently large to admit an end of needle 1 projecting from hub 2. First end 16 of sheath 15 is preferably narrower than sheath 15, with a defined outer diameter d2. A second end 18 of sheath 15 is open, and features a threaded male joint 19. A longitudinal slot 20 extends from a first point near end 16 of the sheath, to the second end 18 of the sheath. Slot 20 is closed at the first point, but is open at the second end of the sheath.

A cap 21 having a threaded female joint is adapted to be screwed onto the male joint 19 of the sheath 15. The cap then acts to close slot 20 at the second end of the sheath. If the housing is intended to be used with a catheter, the second end of sheath 15 may be closed by cap 21. If the housing is intended to be used with a syringe or for blood collection, cap 21 takes the form of a ring having a threaded joint on its inner surface. Cap 21 then closes slot 20 without closing the second end of sheath 15.

Figure 7A:
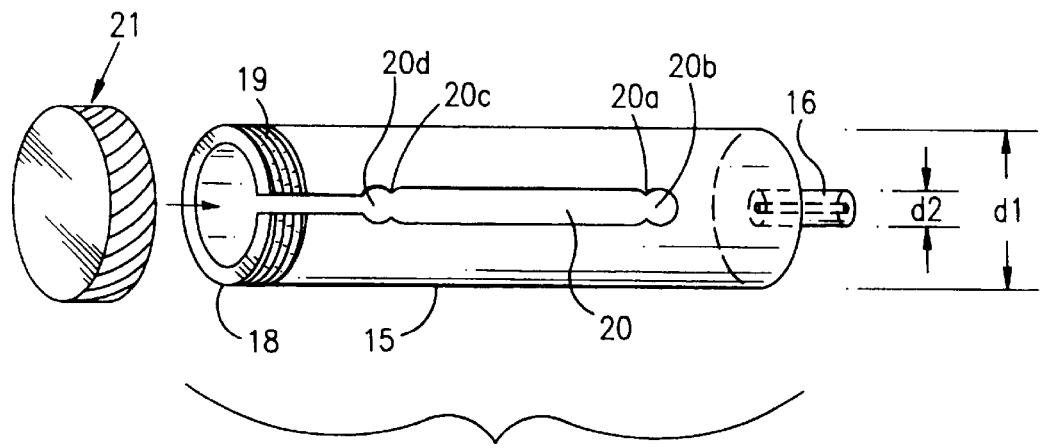
FIGS. 7*a*, 7*b*, and 8 illustrate embodiments of a cylindrical housing for use with a needle assembly.
Figure 7B:
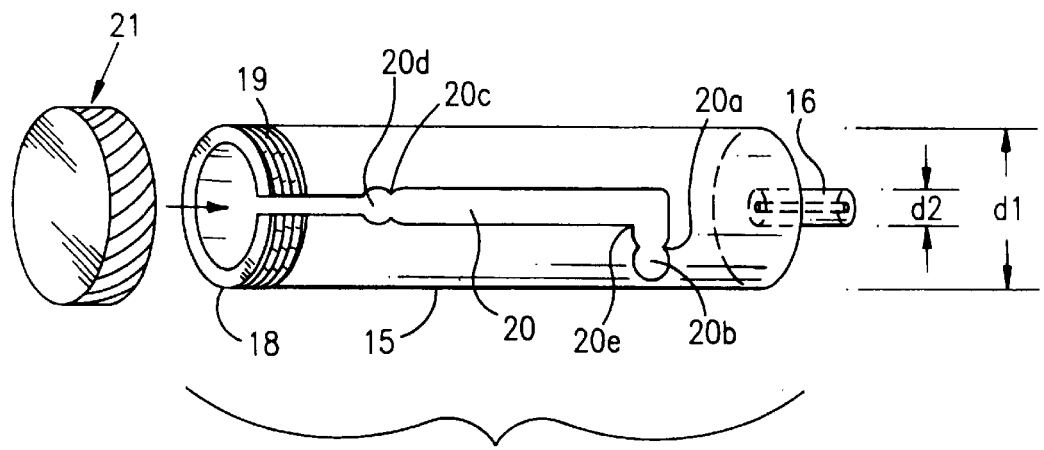

In a first embodiment of the housing, slot 20 is a linear slot with no branches (FIG. 7a). Near the closed end of slot 20, at least one tooth 20a, preferably a pair of teeth 20a on opposite sides of slot 20, causes the width of slot 20 to narrow from a first width which is greater than the diameter of stem 7 to a width which is less than the diameter of stem 7. Between the tooth or teeth 20a and the closed end of slot 20, a first locking position 20b is defined. The first locking position 20b is round, and has a diameter equal to the diameter of stem 7, so as to hold stem 7 tightly in position. If desired, a bend 20e of 90° or more may be included in slot 20 (FIG. 7b), so that the knob has to be pushed around bend 20e in order to reach teeth 20a and locking position 20b. Although not necessary, this has the advantage that locking position 20b has a continuous back wall, making it difficult for the knob to be accidentally pushed out of the locking position 20b when performing a procedure. Similarly, near cap 21, at least one tooth 20c, preferably a pair of teeth 20c on opposite sides of slot 20, causes the width of slot 20 to narrow from a first width which is greater than the diameter of stem 7 to a width which is less than the diameter of stem 7. Between the tooth or teeth 20c and cap 21, a second locking position 20d is defined. The second locking position 20d also has a diameter equal to the diameter of stem 7, so as to hold stem 7 tightly in position.

Figure 8:
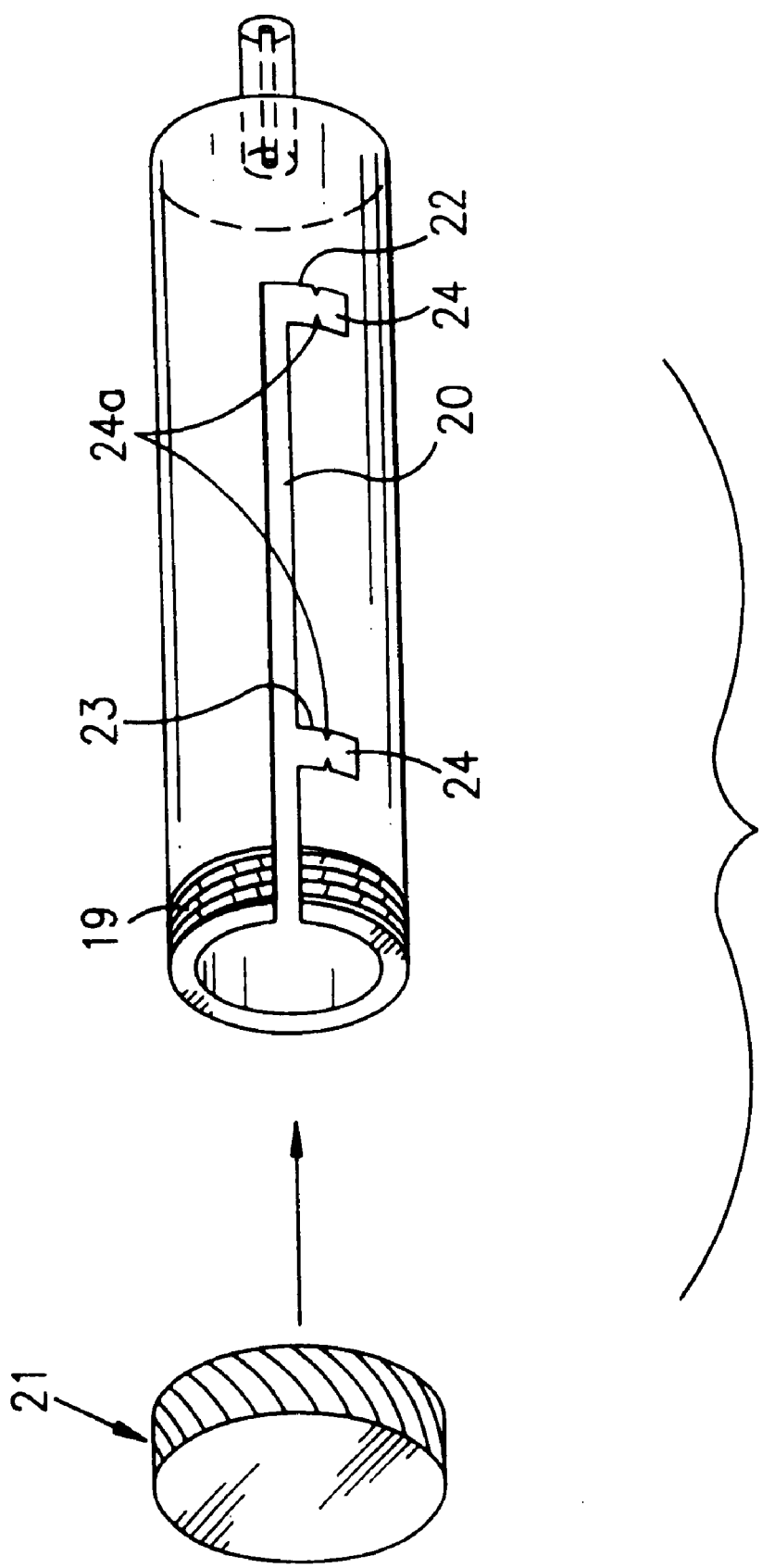

In a second embodiment of the housing, slot 20 is a linear slot having a first transverse branch 22 which intersects slot 20 at the closed end of slot 20, and a second transverse branch 23 which intersects slot 20 near cap 21 (FIG. 8). Slot 20 and branches 22 and 23 are all wider than the diameter of stem 7. A locking position 24 is defined in each of branches 22 and 23. Each branch features at least one tooth 24a, preferably a pair of teeth 24a on opposite sides of the branch, which causes the width of the branch to narrow from a first width which is greater than the diameter of stem 7 to a width which is less than the diameter of stem 7. Locking position 24 is located between the tooth or teeth 24a and the end of the branch.

ASSEMBLY OF A CATHETER INSERTION DEVICE

Figure 9:
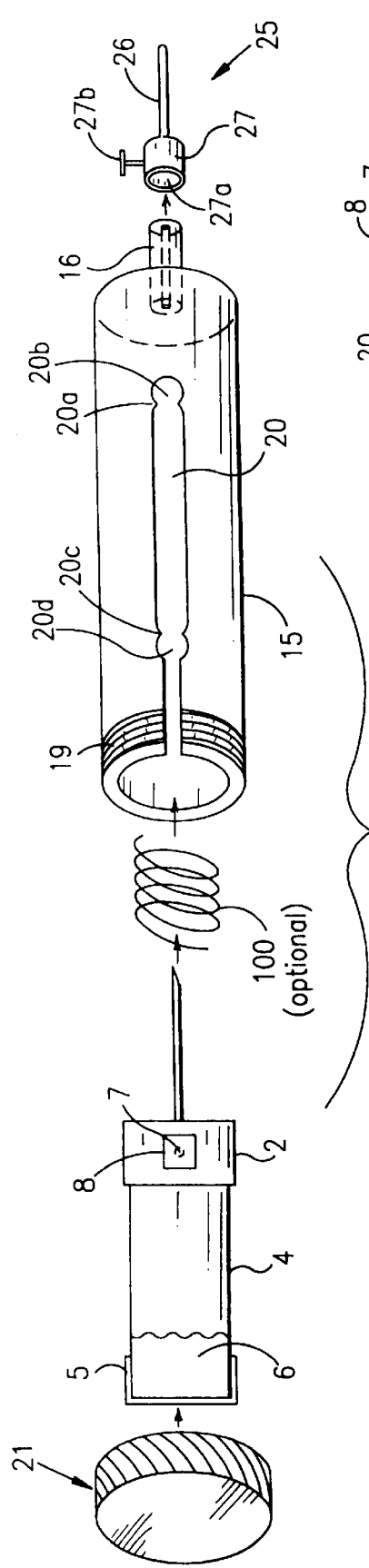
FIGS. 9 and 11 illustrate assembly of a catheter insertion device having a retractable needle.

A catheter insertion device is assembled as shown in the exploded drawing of FIG. 9. The needle assembly of FIG. 1 is inserted into the second end 18 of the sheath 15 of FIG. 7, with needle 1 being directed toward the first end 16 of the sheath and stem 7 being slidably engaged by slot 20. The thumbrest attached to stem 7 is positioned outside the sheath; it is important that the thumbrest be too large to pass through slot 20. The needle assembly slides into sheath 15 until the stem contacts teeth 20c. Teeth 20c should be close enough together to prevent the stem from accidentally passing between teeth 20c, but far enough apart that the stem can be pushed between teeth 20c without undue effort. The distance between teeth 20a should be substantially the same as the distance between teeth 20c. Cap 21 is then screwed onto sheath 15.

At this point, stem 7 is positioned in rear locking position 20d. Needle 1 is contained within the sheath, with the point of needle 1 being positioned in the narrow end 16 of the sheath. The thumbrest 8 may be used to push stem 7 through teeth 20c and forward along slot 20 until it reaches teeth 20a. The thumbrest is then used to push the stem 7 through teeth 20a into locking position 20b. This carries the hub and the needle attached thereto forward in the sheath until needle 1 is exposed through hole 17. The needle is reversibly locked into an exposed position until thumbrest 8 is used to manually push stem 7 past teeth 20a, along slot 20, and past teeth 20c into locking position 20d. This causes the needle to retract into the sheath. If desired, a spring 100 may be positioned between inner surface of the narrow end of sheath 15 and hub 2; the spring acts to bias stem 7 away from locking position 20b toward locking position 20d. Use of the spring is, however, not necessary.

While the needle is locked in its exposed position, a flexible catheter 25 having a hollow cannula 26 and a hub 27 having a cavity 27a adapted to frictionally engage the narrow end of sheath 15 slides over needle 1 until the catheter hub engages the end of sheath 15. Needle 1 supports the catheter in a straightened position, with the tip of needle 1 extending beyond the end of catheter 25. The catheter may be disengaged from the needle and sheath by manually disengaging hub 27 from sheath 23 and withdrawing the needle from the catheter cannula. The used needle may then be retracted into the housing as previously described. A knob 27b may be positioned on the hub 27 to aid in grasping the catheter while disengaging the catheter from the sheath 23.

Figure 10:
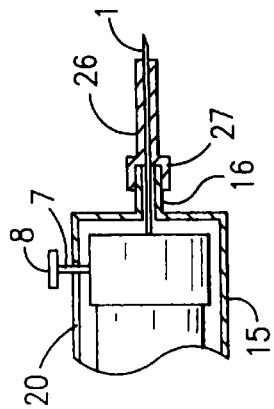
FIG. 10 shows how the catheter engages the catheter insertion device.

Normally, the assembly is sold with the needle in the exposed position and the catheter positioned on the needle (FIG. 10). A plastic cover (not shown) covers the catheter and needle, preventing needle stick injuries. After the cover is removed, the needle may be used to penetrate a patient's skin and enter a blood vessel. The needle is then used to carry the catheter into the blood vessel. When the catheter is positioned in the blood vessel, the needle and sheath assembly is disengaged, as described above.

Figure 11:
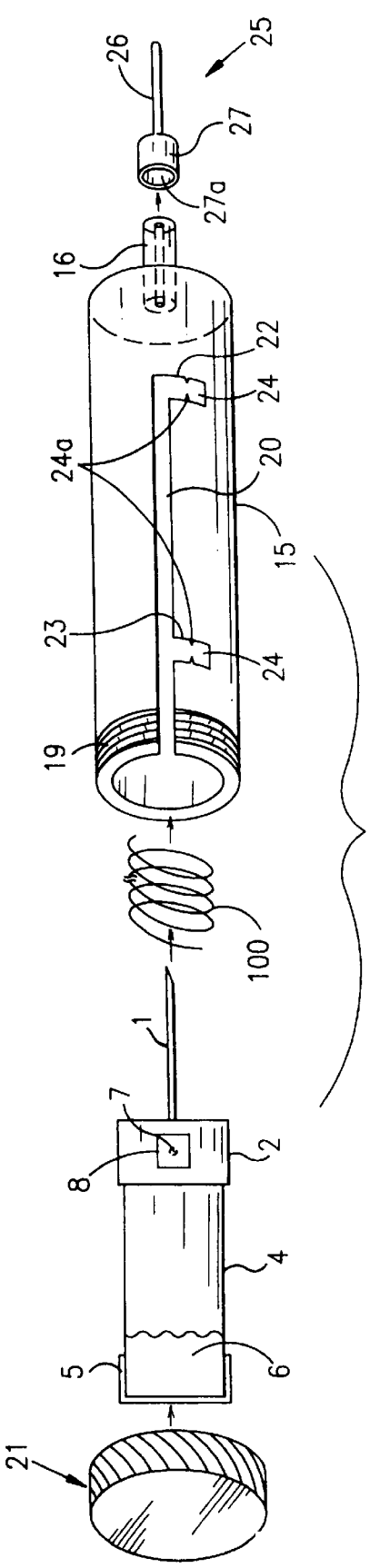

Assembly of a catheter insertion device using the housing of FIG. 8 is carried out in a similar way (FIG. 11). The needle assembly of FIG. 1 is inserted into the second end 18 of the sheath 15 of FIG. 9 with the stem engaging slot 20, exactly as previously described. The needle assembly slides into sheath 15 until the stem reaches the rear transverse branch 23, whereupon the stem is pushed into branch 23 until it contacts teeth 24a. Teeth 24a should be close enough together to prevent the stem from accidentally passing between teeth 24a, but far enough apart that the stem can be pushed between teeth 24a without undue effort. The stem is the pushed through teeth 24a into locking position 24. Cap 21 is then screwed onto sheath 15.

At this point, needle 1 is contained within the sheath, with the point of needle 1 being positioned in the narrow end 16 of the sheath. The thumbrest 8 may be used to push stem 7 back to slot 20, and the thumbrest may then be used to push the stem along slot 20 until it reaches forward branch 22. The thumbrest is then used to push the stem 7 into branch 22 and through teeth 24a into locking position 24. This carries the hub and the needle attached thereto forward in the sheath until needle 1 is exposed through hole 17. The needle is reversibly locked into an exposed position until thumbrest 8 is used to manually push stem 7 back to slot 20 and along slot 20 toward branch 23, causing the needle to retract into the sheath. A spring 100 is positioned between the inner surface of the narrow end of sheath 15 and hub 2; the spring acts to bias stem 7 away from branch 22 toward branch 23. When the stem is in branch 22, the spring acts to lock the stem into position. Once the stem 7 reaches branch 23, it is pushed into branch 23 and through teeth 24a into the second locking position 24. Teeth 24a act to prevent the stem from being dislodged from a locking position 24.

While the needle is locked in its exposed position, a flexible catheter 25 having a hollow cannula 26 and a hub 27 having a cavity 27a adapted to frictionally engage the narrow end of sheath 15 slides over needle 1 until the catheter hub engages the end of sheath 15, exactly as previously described.

RETRACTABLE SYRINGE AND BLOOD COLLECTION NEEDLES

A retractable syringe needle for use with hypodermic syringes is assembled as shown in the exploded drawing of FIG. 12. The needle assembly of FIG. 3 is inserted into the second end 18 of the sheath 15 of FIG. 7, with needle 1 being directed toward the first end 16 of the sheath and stem 7 being slidably engaged by slot 20. The needle assembly slides into sheath 15 until the stem contacts teeth 20c. Teeth 20c should be close enough together to prevent the stem from accidentally passing between teeth 20c, but far enough apart that the stem can be pushed between teeth 20c without undue effort. The distance between teeth 20a should be substantially the same as the distance between teeth 20c. A ring-shaped cap 21 is then screwed onto sheath 15.

At this point, stem 7 is positioned in rear locking position 20d (FIG. 13a). Needle 1 is contained within the sheath, with the point of needle 1 being positioned in the narrow end 16 of the sheath. The thumbrest 8 may be used to push stem 7 through teeth 20c and forward along slot 20 until it reaches teeth 20a. The thumbrest is then used to push the stem 7 through teeth 20a into locking position 20b. This carries the hub and the needle attached thereto forward in the sheath until needle 1 is exposed through hole 17 (FIG. 13b). The needle is reversibly locked into an exposed position until thumbrest 8 is used to manually push stem 7 past teeth 20a, along slot 20, and past teeth 20c into locking position 20d. Since the slot 20 is wider than stem 7, this is quickly done with the application of minimal force, except when pushing the stem past the teeth. This causes the needle to retract into the sheath. If desired, a spring 100 (not shown) may be positioned between inner surface of the narrow end of sheath 15 and hub 2; the spring acts to bias stem 7 away from locking position 20b toward locking position 20d after it has been pushed through teeth 20a and out of locking position 20b. Again, use of the spring is not necessary.

Normally, the assembly is sold with the needle in the retracted position (FIG. 13a). Plastic covers (not shown) may be used to cover the opening in ring-shaped cap 21 and opening 17 of the housing, preventing needle stick injuries. After the covers are removed, the frusto-conical tip of a syringe barrel 28 is fitted into cavity 9 of hub 2. Cavity 9 engages the tip of barrel 28 releasably, by means of friction. The syringe barrel should be of a size that allows the housing sheath 15 to slide over the syringe barrel. The retracted needle is then exposed, as previously described (FIG. 13b). This causes hub 2 to move toward opening 17 of the housing, and also causes 28 to enter the housing. The hypodermic needle may then be used to administer an injection to a patient, or to withdraw fluid samples from a patient's body. Once the needle has been used, the needle may be retracted into the housing, and the syringe barrel may be disengaged from the cavity in hub 2.

Figure 14:
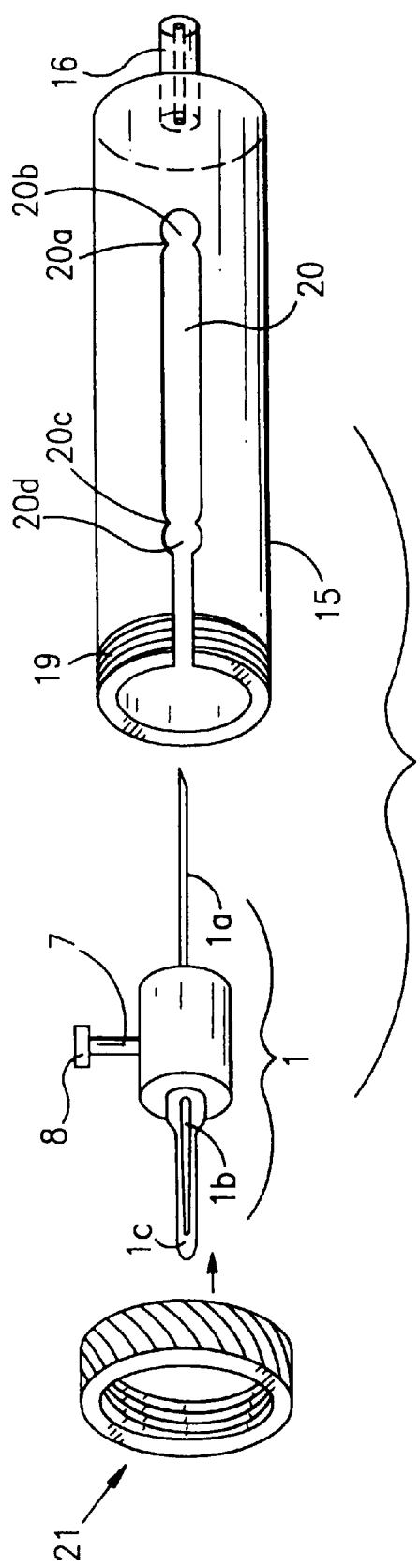
FIG. 14 illustrates assembly of a retractable needle for use in obtaining blood samples.

A retractable needle for use in collecting blood samples is assembled as shown in the exploded drawing of FIG. 14. The needle assembly of FIG. 2 is inserted into the second end 18 of the sheath 15 of FIG. 7, with needle end 1a being directed toward the first end 16 of the sheath and stem 7 being slidably engaged by slot 20. Needle end 1b, covered by the elastomeric sheath, is directed toward the threaded end of sheath 15. The needle assembly slides into sheath 15 until the stem contacts teeth 20c. Teeth 20c should be close enough together to prevent the stem from accidentally passing between teeth 20c, but far enough apart that the stem can be pushed between teeth 20c without undue effort. The distance between teeth 20a should be substantially the same as the distance between teeth 20c. A ring-shaped cap 21 is then screwed onto sheath 15.

At this point, stem 7 is positioned in rear locking position 20d. Needle 1 is contained within the sheath, with the point of needle 1 being positioned in the narrow end 16 of the sheath. The thumbrest 8 may be used to push stem 7 through teeth 20c and forward along slot 20 until it reaches teeth 20a. The thumbrest is then used to push the stem 7 through teeth 20a into locking position 20b. This carries the hub and the needle attached thereto forward in the sheath until needle 1 is exposed through hole 17. The needle is reversibly locked into an exposed position until thumbrest 8 is used to manually push stem 7 past teeth 20a, along slot 20, and past teeth 20c into locking position 20d. This causes the needle to retract into the sheath. Again, a spring (not shown) may, if desired, be used to bias stem 7 toward locking position 20d.

Figure 15:
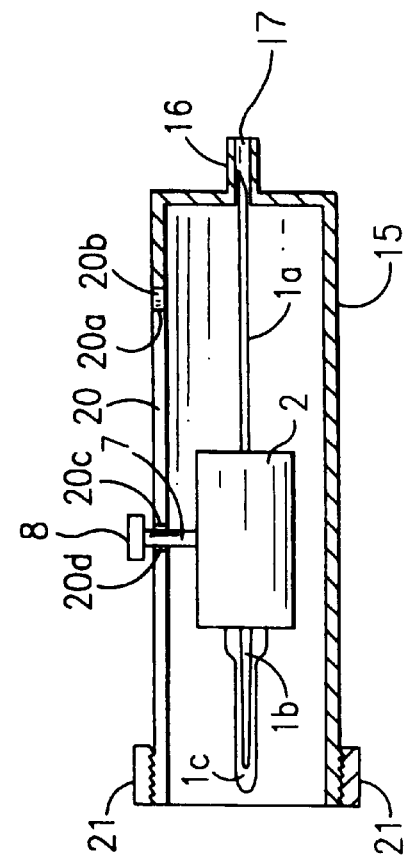
FIG. 15 illustrates the assembled retractable needle for use in obtaining blood

Normally, the assembly is sold with the needle in the retracted position (FIG. 15). Plastic covers (not shown) may be used to cover the opening in ring-shaped cap 21 and opening 17 of the housing, preventing needle stick injuries. After the covers are removed, end 1a of the retracted needle may then be exposed, as previously described. This causes hub 2 to move toward opening 17 of the housing. Once the needle has been exposed, the needle may be inserted through a patient's skin and into a blood vessel. At this point, the sheath on needle end 1b prevents blood from flowing from the blood vessel and through the needle 1. An evacuated test tube 29 having an elastomeric cover over its open end may then be inserted into the larger end of sheath 15, with the elastomeric cover being directed toward needle end 1b. When the cover on the test tube is pushed against needle end 1b, the needle penetrates the elastomeric sheath covering the needle and the cover on the test tube. This places the interior of the evacuated tube in fluid communication with the blood vessel, allowing blood to flow from the vessel into the tube 29. Once the needle has been used has been used to collect a blood sample, the test tube may be removed. The eleastomeric sheath on the needle then recovers needle end 1b, cutting off further blood flow. The needle may then be retracted into the housing.

The housing of FIG. 8 may also be used to construct a retractable needle for use in collecting blood samples or a retractable syringe needle for use with hypodermic syringes, in much the same way that it was used to construct an alternate version of the catheter insertion assembly of FIG. 9.

In all of the above devices, including the catheter insertion devices, the retractable syringe needles, and the needles for collection of blood samples, hub 2 of the needle should be maintained at a position which aligns the needle passing therethrough along the axis of sheath 15. This makes it easier to expose the needle quickly. Normally, the needle is coaxial with the hub, so the hub may be maintained along the axis of the sheath by setting the inner diameter of the sheath to be equal to the maximum diameter of the hub. Alternatively, the stem 7 may be constructed so that the distance along the stem from the hub 7 to the thumbrest 8 is equal to the difference between the inner radius of sheath 15 and the maximum radius of hub 7. This ensures that the sheath and the hub are coaxial.

Figure 16:
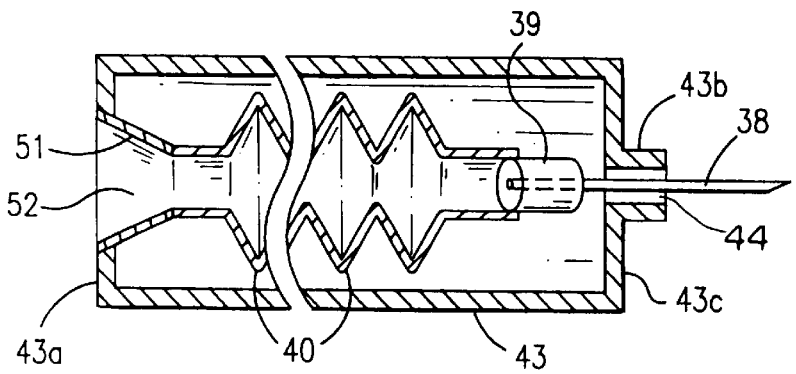
FIG. 16 illustrates a retractable syringe needle having an adjustable-length tube.

A further embodiment of the invention will now be discussed. The second embodiment of the retractable syringe needle features a hypodermic needle assembly similar to that shown in FIG. 1 for use in the first embodiment. The needle assembly, shown in FIG. 16, features a hollow hypodermic needle 38 and a cylindrical hub 39 having an axial passage therethrough. The hollow needle is rigidly connected with the hub so that the axial passage and the interior of the hollow needle form a continuous conduit. Hub 39 is secured to one end of an adjustable-length tube 40 so that the interior of hollow needle 38 makes fluid contact with the interior of tube 40. Tube 40 is preferably impermeable to liquids, non-elastic, and axially collapsible. By collapsing the tube in an axial direction, the length of tube 40 may be changed from a first extended length to a second contracted length. The tube may then be extended in an axial direction, restoring the length of the tube to the first extended length.

A tubular sheath 43 is disposed around the adjustable-length tube 40. The tubular sheath 43 has a first end 43a which is rigidly connected with the first end of the adjustable-length tube and a second end 43b having an opening 44 which is sufficiently large to allow the end of the hypodermic needle 38 to pass therethrough. The outer surface of member 51 is rigidly secured to end 43a of sheath 43. When the apparatus is not in use, the opening at each end of the tubular sheath may be covered by a cap (not shown in the drawings). The caps may screw onto the sheath, or snap onto the sheath.

Figure 17A:
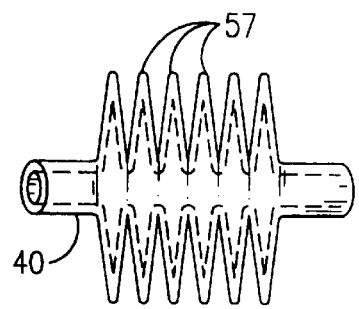
FIGS. 17*a*, 17*b*, 18*a*, and 18*b* show two types of adjustable-length tubes which may be used with the needle of FIG. 16.
Figure 17B:
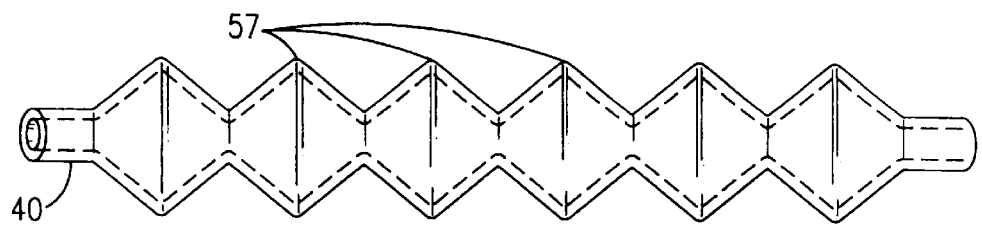

The preferred embodiments of the adjustable-length tube 40 will now be discussed. The most preferred type of adjustable-length tube 40 contemplated for use in this invention features a series of circumferential pleats 57 disposed along the length of the tube, as shown in FIGS. 17a and 17b. When tube 40 is in its contracted or collapsed state (FIG. 17a), pleats 57 are folded together. The adjustable-length tube may be lengthened by pulling one end of tube 40 (the end to which the hub is attached) away from the other, causing pleats 57 to unfold (FIG. 17b).

Figure 18A:
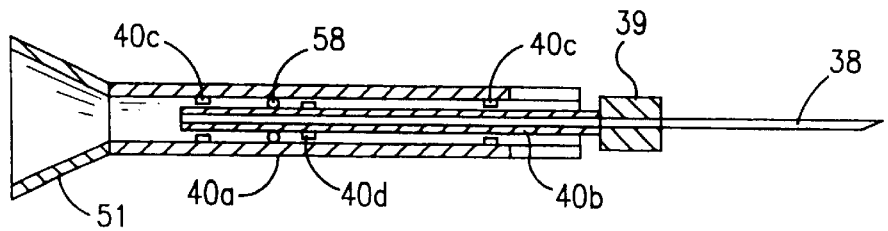
Figure 18B:
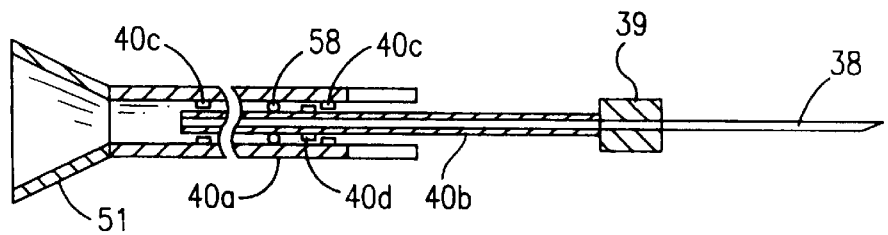

Another embodiment of adjustable-length tube 40 is a telescoping tube made from an outer tube 40a and an inner tube 40b, as shown in FIGS. 18a and 18b. The inner tube is slidably disposed within the outer tube. A first end of outer tube 40a is adapted to be secured to syringe barrel 40 through conical member 51, as previously described. A first end of inner tube 40b is adapted to be secured to hub 39. The inner tube 40b may be moved from a position where tube 40b is entirely or primarily disposed within tube 40a (FIG. 18a), contracting tube 40, to a position where tube 40b is mostly exposed (FIG. 18b), expanding tube 40. Ridges 40c on the interior of outer tube 40a interact with a ridge 40d on the outer surface of tube 40b, acting as stops to prevent removal of tube 40b from tube 40a. Preferably, a leakproof sealing material 58 is disposed between the outer surface of the inner tube and the inner surface of the outer tube. This sealing material may be a hydrophobic, biocompatible polymer with a low coefficient of friction, such as silicone or teflon.

Figure 19A:
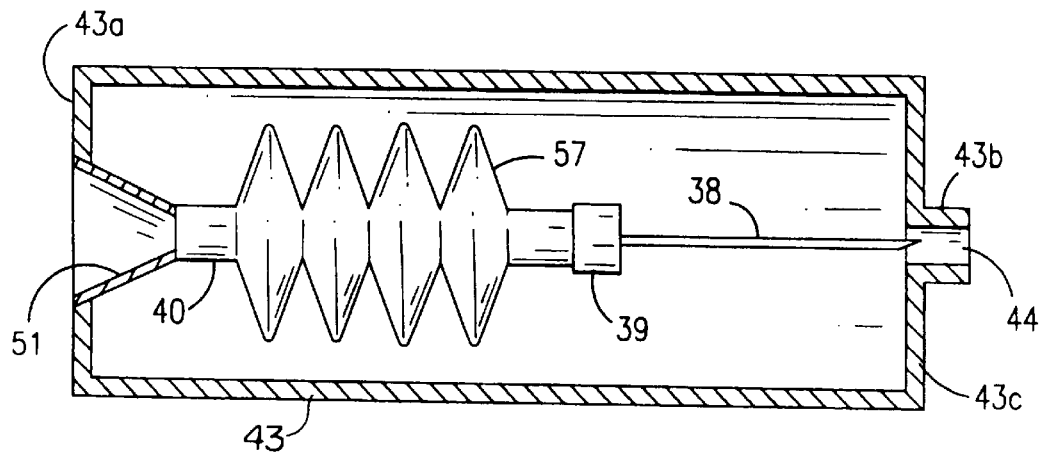
FIGS. 19*a* and 19*b* illustrate a retractable syringe needle having an adjustable-length tube in its retracted state and in its expanded state, respectively.
Figure 19B:
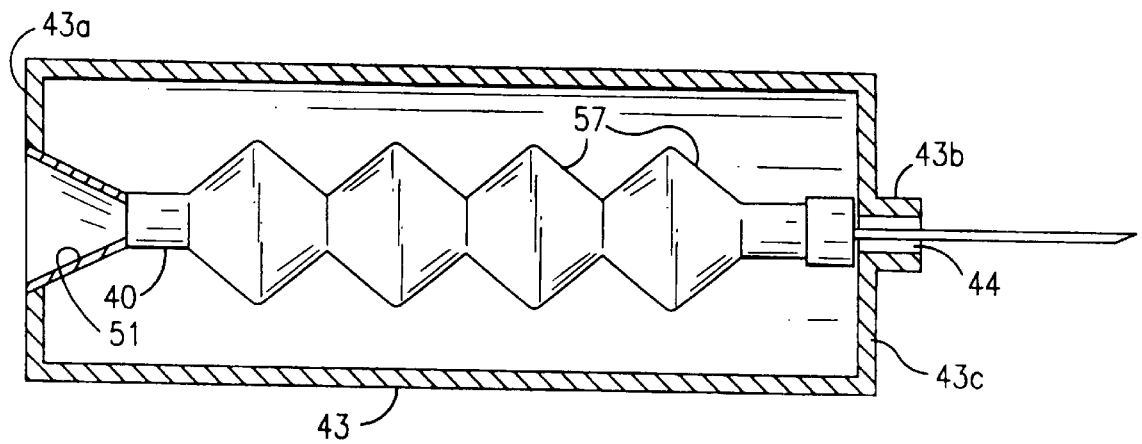

When the adjustable-length tube is contracted, the hypodermic needle is entirely disposed within the sheath (FIG. 19a). When the adjustable-length tube is extended, the end of the hypodermic needle is exposed through opening 44 in the second end of the sheath (FIG. 19b). If desired, the interior diameter of the sheath 43 may narrow from a diameter which is great enough to receive the adjustable-length tube 40 to a diameter which is little greater than the diameter of needle 1. This narrowing occurs at a point 43c near the opening 44. When the needle is disposed within the sheath, the pointed end of the needle then occupies a position where the inner diameter of the container is small (FIG. 19a). This helps prevent the needle point from moving away from the axis of the container.

Figure 20:
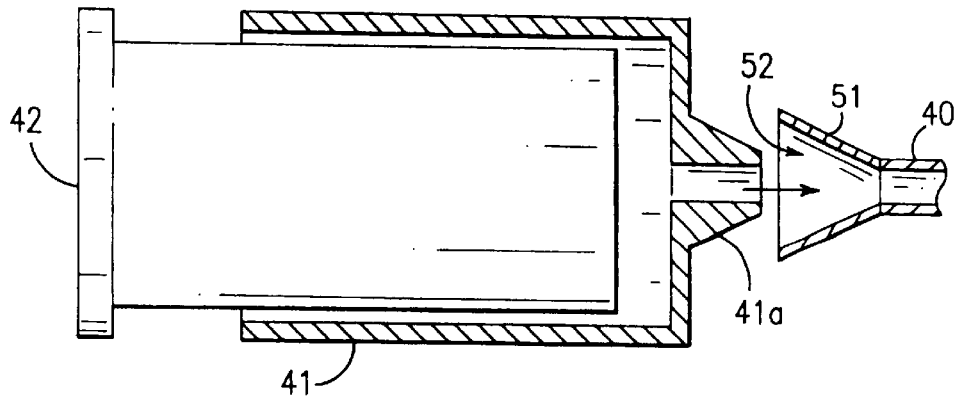
FIG. 20 shows illustrates attachment of a syringe to an adjustable-length tube.

This embodiment of the invention may be used to withdraw fluid samples from a patient's bloodstream, or to inject medicinal fluids into a patient's bloodstream. A syringe barrel 41 having a plunger 42 slidably mounted therein may be reversibly secured to the other end of the adjustable-length tube 40 so that the interior of the syringe barrel is in fluid contact with the interior of the adjustable-length tube, as shown in FIG. 20. By raising the plunger and creating a partial vacuum within barrel 41, fluids may then be drawn through needle 38 (not shown in FIG. 20) and tube 40 into barrel 41. The syringe barrel 41 is secured to the first end of the adjustable-length tube 40 by means of a hollow conical member 51. The inner surface of member 51 defines a frustoconical cavity 52 adapted to frictionally engage a frustoconical tip 41a of the syringe barrel. The conical member 51 has a narrow end with a passage 51a therethrough. The narrow end of member 51 is connected to the end of the adjustable-length tube 40 to which hub 39 is not secured. The frustoconical 52 cavity makes fluid contact with the interior of the adjustable-length tube 40 through the passage 51a. As the outer surface of member 51 is rigidly secured to the first end of the tubular sheath 43 (sheath 43 is not shown in FIG. 21), sheath 43 is immobile relative to a syringe barrel 41 connected to tube 40.

Figure 21A:
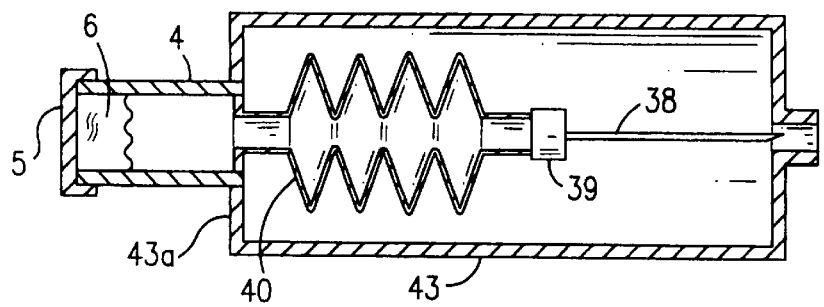
FIGS. 21a and 21b show a catheter insertion device having an adjustable-length tube.
Figure 21B:
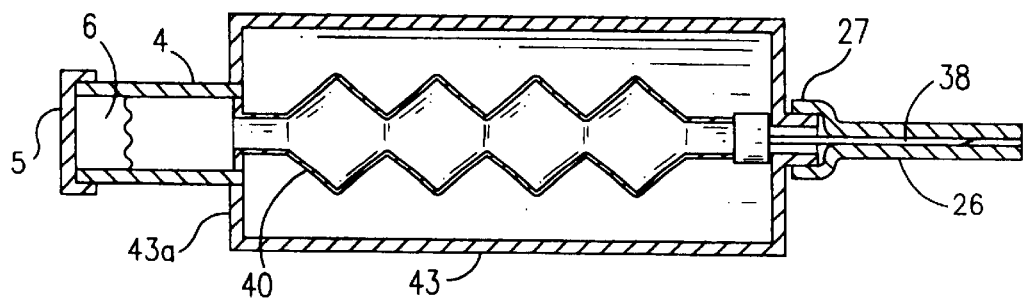

Alternatively, a flash chamber may be present instead of conical member 51, allowing the needle to be used with a catheter (FIG. 21a). The flash chamber comprises a tubular side wall 4 having a first end which makes a watertight seal with the opposite end of tube 40 from that to which hub 39 is attached. Cap 5 closes the second end of tabular wall 4, making a second leakproof seal The interior of flash chamber 3 is in fluid communication with the interior of hollow needle 38 and tube 40, so that fluid may travel through the needle 38 and tube 40 into chamber 3. Additionally, tubular wall 4 is rigidly secured to end 43a of sheath 43. The tubular wall of chamber 3 is normally transparent or translucent, so that blood entering the flash chamber through needle 1 is readily visible. A small plug of cotton 6 is normally present in flash chamber 3, just under cap 5, although this is not an essential feature of the invention. In this embodiment, the needle is normally sold in the exposed position with a catheter positioned on the needle (FIG. 21b), where the catheter features a cannula 26 which encases the needle, and a hub 27 which is detachably secured to end 43b of the sheath. After the catheter is inserted into a blood vessel, the needle is withdrawn from the catheter, and the used needle is withdrawn into sheath 43 by contracting the adjustable-length tube.

Figure 22:
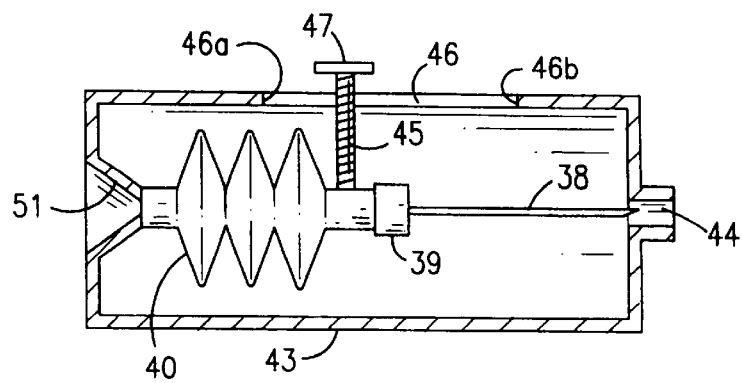
FIGS. 22, 24, 24a and 25 illustrate mechanisms for controlling the length of the adjustable-length tube.
Figure 23:
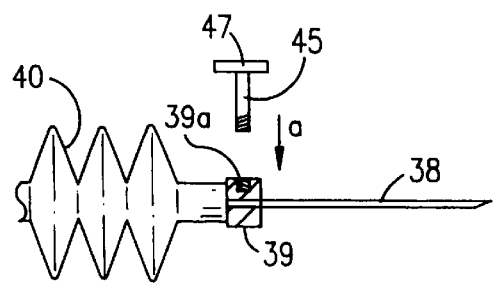
FIGS. 23, 26, 27a, and 27b show assembly of a retractable syringe needle having the adjustable-length tube.

The second embodiment of the invention additionally features a mechanism allowing the user to reversibly alter the length of the adjustable-length tube from the contracted length to the extended length at will. This mechanism is substantially the same whether the needle is used with a syringe or with a catheter, and features a knob 45 which is rigidly connected with hub 39, as shown in FIGS. 22. The knob 45 may be indirectly connected to hub 39 by connecting knob 45 to the end of tube 40 to which hub 39 is attached, as in FIG. 22, or it may be directly attached to hub 39. The knob 45 may be connected with the hub 39 by inserting the end of the knob into a hole 39a in the hub, and securing the knob into position by means of an adhesive, as shown in FIG. 23. Alternatively, the knob is connected with the hub by screwing a threaded male joint on the knob into hole 39a, where hole 39a is a threaded female joint on the hub 39. If extra security is desired, knob 45 may be connected with the hub by applying an adhesive to either of the threaded male joint or the threaded female joint (or both of the threaded joints), screwing the threaded male joint into the threaded female joint on the hub, and allowing the adhesive to bond the male joint to the female joint. Similar methods may be used to secure the knob to the end of tube 40.

Figure 24:
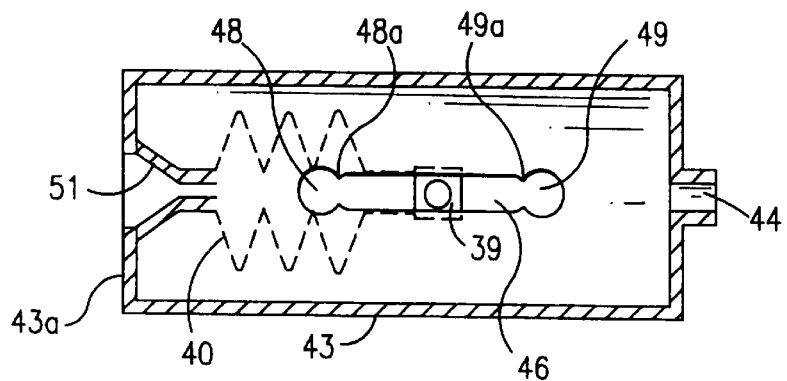
Figure 24A:
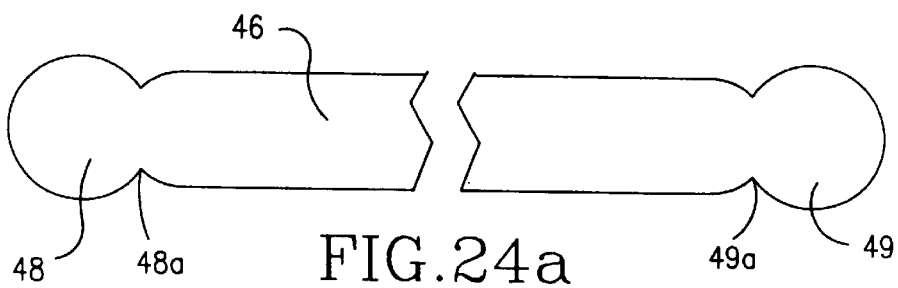

The knob 39 slidably engages a longitudinal slot 46 which is wider than the diameter of knob 45 running along the length of the tubular sheath 43 (FIG. 22). Preferably, slot 46 is closed at both ends (FIG. 24; tube 40 and hub 39 shown in broken lines)). Thumbrest 47 (not shown) is accessible from outside sheath 43, and may be used to reversibly slide the knob from a first position 46a along the length of the longitudinal slot to a second position 46b along the length of the longitudinal slot, nearer opening 44 than the first position. When the knob is in the first position, the adjustable-length tube is contracted and the needle 38 is concealed within sheath 43. Sliding the knob into the second position causes the adjustable-length tube to extend, allowing the needle 38 to emerge through opening 44 in sheath 43. When the tube is contracted and the needle is concealed, caps may be used to cover the openings in the ends of the tubes. The shape of the slot is shown in detail in FIG. 24a.

The knob may be reversibly secured at the first position along the length of the longitudinal slot 46, maintaining tube 40 in a contracted state. This may be done by pushing knob 45 past teeth 48a, which are positioned on opposite sides of the longitudinal slot near the first position 46a. Teeth 48a cause the width of the slot to narrow from greater than the diameter of knob 45 to a width which is sufficiently less than the diameter of knob 45 to prevent the knob from accidentally passing between the teeth 48a, but which is large enough to allow the user to use thumbrest 47 to manually push knob 45 between teeth 48a. Once the knob passes teeth 48a, it enters locking position 48, a round hole through the sheath which grips knob 45, holding it in the first position. The locking position has a diameter which is equal to the diameter of the knob. Similarly, the knob may be reversibly securing at the second position along the length of the longitudinal slot 46, when tube 40 is extended, by pushing knob 45 past teeth 49a, which are positioned on opposite sides of the longitudinal slot near the second position in FIG. 23. Teeth 49a, like teeth 48a, cause the width of the slot to narrow from greater than the diameter of knob 45 to a width which is less than the diameter of knob 45, but which is large enough to allow the user to use thumbrest 47 to manually push knob 45 between teeth 49a. Once the knob passes teeth 49a, it enters locking position 49, a round hole through the sheath which grips knob 45. The locking position has a diameter which is equal to the diameter of the knob.

Figure 25:
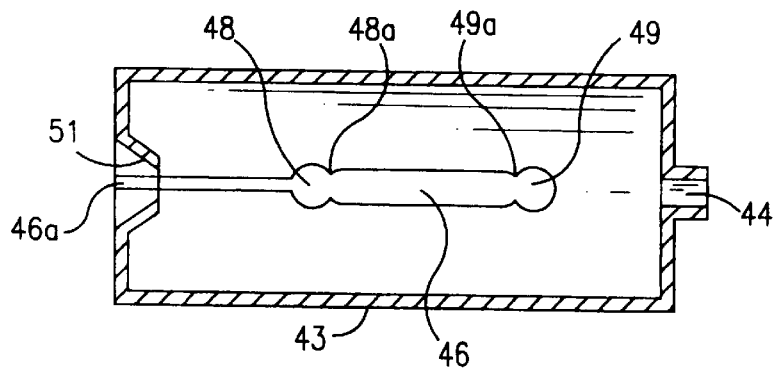
Figure 26:
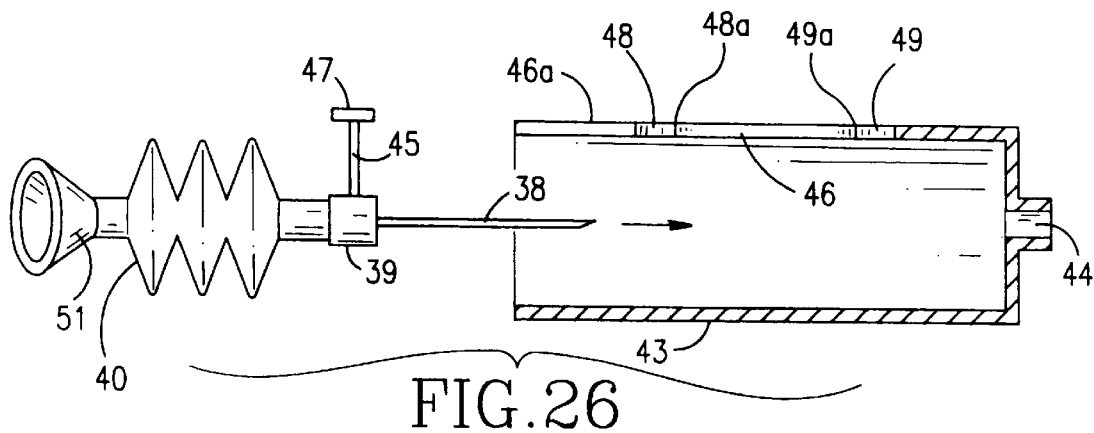
Figure 27A:
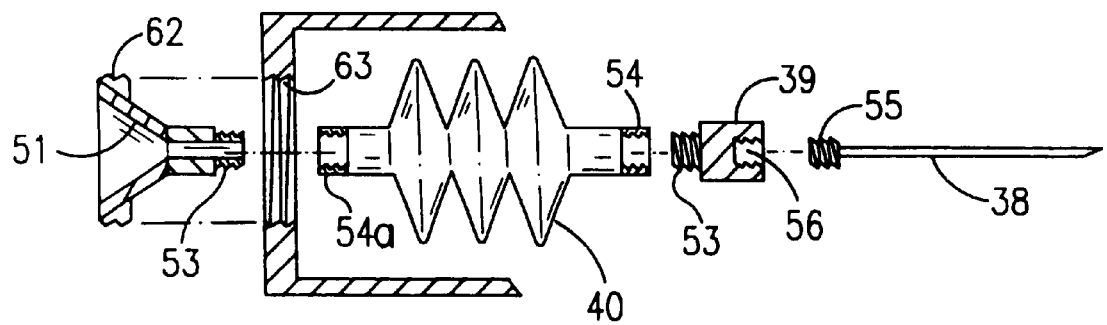

In a slightly different embodiment of the tubular sheath, shown in FIG. 25, the longitudinal slot is open-ended, with a branch 46a extending from locking position 49 to the end of the tubular sheath which is connected to the adjustable-length tube. In the embodiment adapted to receive the syringe in conical member 51, the knob engaging the slot is prevented from passing through the open end of the slot by hollow conical member 51, which is rigidly secured to the inner surface of the sheath. The assembly may be manufactured by sliding the hub having the pin connected thereto into the sheath so that the knob slides into the open end of the slot. The adjustable-length tube is connected to the hub at on end, and to conical member 51 at the other. The adjustable-length tube slides into the sheath, and member 51 is then secured to the inner surface of the sheath, as shown in FIG. 26. The hub 39 may be secured to one end of the adjustable-length tube 40 in the following manner (FIG. 27a). A male joint 53 is provided on one end of the hub, opposing needle 38. A female joint 54 is provided on one end of the tube 40. The male joint on the hub is then secured to the female joint on tube 40 so as to provide a leakproof seal, as shown in the exploded view of FIG. 26. One way of doing this is to provide a threaded male joint on the hub, and a threaded female joint on the adjustable-length tube, as shown in the figure. The male and female joints may then be screwed together. Alternatively, a waterproof and biocompatible adhesive material may be used to secure the female joint to the male joint.

A female joint 54a on the other end of tube 40 is secured to a male joint 53a on the narrow end of conical, syringe-receiving member 51. The method of doing this is not particularly limited. The end of part 40 may be adhesively bonded to the outer surface of part 51. Also, a threaded male joint on the outer surface of part 51 may be screwed into a threaded female joint on the inner surface of part 61.

Figure 27B:
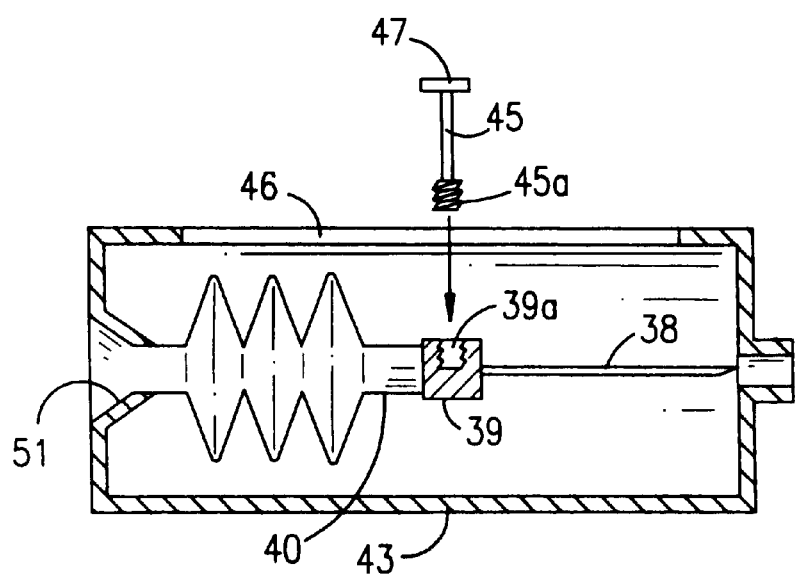

Similarly, needle 38 may be secured to hub 39 by providing a male joint 55 on one end of the needle 38 (also shown in FIG. 27a). A female joint 56 is provided on the hub, opposing the male joint 53 for attachment to tube 40. The female joint on the hub is then secured to the male joint on needle 38 so as to provide a leakproof seal. One way of doing this is to provide a threaded female joint 56 on the hub, and a threaded male joint 55 on the needle, as in FIG. 24. Joints 55 and 56 may then be screwed together. Alternatively, a waterproof and biocompatible adhesive material may be used to secure the female joint 56 to the male joint 55. An additional possibility is that the hub may be molded around the needle 38. Also (FIG. 27b), the knob 45 may be secured to hub 39 by passing a threaded joint 45a on the knob through slot 46 and screwing joint 45a into a threaded joint 39a on the hub.

The first open end 43a of tubular sheath 43 is secured to conical, syringe-receiving member 51 (FIG. 27a). The method of doing this is not particularly limited. The open end 43a of part 43 may be adhesively bonded to the outer surface of part 51. Also, a threaded male joint 62 on the broad end of the outer surface of part 51 may be screwed into a threaded female joint 63 on the inner surface of part 43 (see FIG. 27a). The embodiment with the catheter is assembled similarly, except that tube 40 is secured to one end of the flash chamber, and the flash chamber is then secured to a joint on sheath 43.

What is claimed is:

1. A retractable needle in combination with a catheter, comprising:
   a) a needle assembly comprising:
      a cylindrical hub having an anterior end and a posterior end;
      a hollow needle extending through the hub and projecting from the anterior end of the hub;
      a tubular flash chamber having a first end which is connected in a leakproof fashion with the posterior end of the hub, and a second end; and
      a stem having a defined diameter rigidly connected with said hub, said stem being non-rotatable relative to said hub, wherein said stem has a thumbrest rigidly fixed to the stem at a defined distance from the hub;
      where an interior of the hollow needle is in fluid communication with an interior of said tubular flash chamber;
   b) a housing with a defined longitudinal axis having a tubular wall with a longitudinal slot which is wider than the diameter of the stem therein, said housing having a first end and a second end, wherein the first end of the housing has an opening adapted to allow the hollow needle to pass therethrough and the second end of the housing is closed;
      said housing having said needle assembly mounted therein so that the stem is slidably engaged by the longitudinal slot, so that said needle assembly may be moved from a first position where the needle passes through the opening in the first end of the housing and is exposed to a second position where the needle is within the housing by sliding the stem toward the second end of the housing and causing the needle to retract through the opening in the first end of the housing;
   c) a means for reversibly locking the stem at a first defined location in said longitudinal slot so as to hold said needle assembly in said first position;
      wherein the means for reversibly locking the stem at the first defined location comprises a first transverse slot intersecting the longitudinal slot at the first defined location, and a first pair of teeth on opposite sides of the first transverse slot; wherein a locking position is defined between the first pair of teeth and a closed end of the first transverse slot; and wherein the first pair of teeth are separated by a distance which is smaller than the diameter of the stem, but which is large enough to allow a user to push the stem through the first pair of teeth;

d) a means for reversibly locking the stem at a second defined location in said longitudinal slot so as to hold said needle assembly in said second position;

e) a catheter which is supported by the needle when the needle is in the first position; and f) a means for removably fastening the catheter to the first end of the housing;

where the hub of said needle assembly is movably positioned along the defined longitudinal axis of the housing.

2. The retractable needle of claim 1, wherein the housing is manufactured from two parts.

3. The retractable needle of claim 2, wherein the housing is manufactured from:

a first part, comprising a hollow tube having a first end adapted to admit the hollow needle and a second end adapted to admit the needle assembly, said second end having a male joint on its outer surface; and a second part, comprising a cap having a female joint adapted to be fitted onto the male joint;

wherein the longitudinal slot in the housing runs along the length of the hollow tube from the first defined location near the first end of the hollow tube to the second end of the hollow tube, with the longitudinal slot being closed at the first end of the hollow tube and having an opening at the second end of the hollow tube, said opening being adapted to admit the stem on the needle assembly;

and wherein the longitudinal slot comprises the means for reversibly locking the stem at the first defined location near the first end of the hollow tube, and the means for reversibly locking the stem at the second defined location near the second end of the hollow tube.

4. The retractable needle of claim 3, wherein the cap is fitted onto the joint at the second end of the hollow tube and acts to close the opening in the longitudinal slot.

5. The apparatus of claim 4, wherein the means for reversibly locking the stem at the second defined location comprises a second transverse slot intersecting the longitudinal slot at the second defined location, and a second pair of teeth on opposite sides of the second transverse slot; wherein a second locking position is defined between the second pair of teeth and a closed end of the second transverse slot; and wherein the second pair of teeth are separated by a distance which is smaller than the diameter of the stem, but which is large enough to allow a user to push the stem through the second pair of teeth.

6. The apparatus of claim 5, wherein a spring acts to bias the stem away from the first defined location toward the second defined location.

7. The apparatus of claim 4, wherein the means for reversibly locking the stem at the second defined location comprises a second pair of teeth on opposite sides of the longitudinal slot at the second defined location; wherein a second locking position is defined by the second pair of teeth and the cap closing the open end of the longitudinal slot; and wherein the second pair of teeth are separated by a distance which is smaller than the diameter of the stem, but which is large enough to allow a user to push the stem through the second pair of teeth.

8. The apparatus of claim 7, wherein a spring acts to bias the stem away from the first defined location toward the second defined location.

9. The retractable needle of claim 4, wherein the means for reversibly locking the stem at the second defined location comprises a second pair of teeth on opposite sides of the longitudinal slot, said second pair of teeth being positioned near the second defined location; wherein a second locking position is defined between the second pair of teeth and the cap fitted onto the joint at the second end of the hollow tube.

10. The apparatus of claim 1, wherein the hub has a diameter which is the same as an inner diameter of the housing.

11. The apparatus of claim 1, wherein the hub has a diameter which is less than an inner diameter of the housing.

12. The apparatus of claim 11, wherein the thumbrest is positioned outside of the housing, and is too wide to pass through the longitudinal slot engaging the stem, and wherein the stem connecting the thumbrest to the hub is sufficiently long to allow the hub to be positioned along the longitudinal axis of the housing.

13. The apparatus of claim 1, wherein the thumbrest is planar.

14. The apparatus of claim 1, wherein the thumbrest is a ring around the tubular housing.

15. A retractable needle, comprising:

a) a needle assembly comprising:

a cylindrical hub having an anterior end and a posterior end, said posterior end of said hub having a frusto-conical cavity therein, said cavity being adapted to frictionally engage a fitting on a syringe barrel;

a hollow needle extending through the hub and projecting from the anterior end of the hub; and a stem having a defined diameter connected with said hub, said stem having a thumbrest rigidly fixed to the stem at a defined distance from the hub;

b) a housing with a defined longitudinal axis having a tubular wall with a longitudinal slot which is wider than the diameter of the stem therein, said housing having a first end and a second end, wherein the first end has an opening adapted to allow the hollow needle to pass therethrough and the second end has an opening adapted to admit the syringe barrel;

said housing having said needle assembly mounted therein so that the stem is slidably engaged by the longitudinal slot, so that said needle assembly may be moved from a first position where the needle passes through the opening in the first end of the housing and is exposed to a second position where the needle is within the housing by sliding the stem toward the second end of the housing and causing the needle to retract through the opening in the first end of the housing;

c) a means for reversibly locking the stem at a first defined location in said longitudinal slot so as to hold said needle assembly in said first position;

d) a means for reversibly locking the stem at a second defined location in said longitudinal slot so as to hold said needle assembly in said second position; and where the hub of said needle assembly is movably positioned along the defined longitudinal axis of the housing.

16. The retractable needle of claim 15, wherein the housing is manufactured from two parts, comprising a hollow tube having a first end adapted to admit the hollow needle and a second end adapted to admit the needle assembly, said second end having a male joint on its outer surface; and a ring having a female joint adapted to be fitted onto the male joint.

17. The apparatus of claim 15, wherein the thumbrest is planar.

18. The apparatus of claim 15, wherein the thumbrest is a ring around the tubular housing.

19. A retractable needle, comprising:
   a) a needle assembly comprising:
      a cylindrical hub having an anterior end and a posterior end, said posterior end of said hub having a frusto-conical cavity therein, said cavity being adapted to frictionally engage a fitting on a syringe barrel;
      a hollow needle extending through the hub and projecting from the anterior end of the hub; and
      a stem having a defined diameter connected with said hub, said stem having a thumbrest rigidly fixed to the stem at a defined distance from the hub;
   b) a housing with a defined longitudinal axis having a tubular wall with a longitudinal slot which is wider than the diameter of the stem therein, said housing having a first end and a second end, wherein the first end has an opening adapted to allow the hollow needle to pass therethrough and the second end has an opening adapted to admit the syringe barrel;
      said housing having said needle assembly mounted therein so that the stem is slidably engaged by the longitudinal slot, so that said needle assembly may be moved from a first position where the needle passes through the opening in the first end of the housing and is exposed to a second position where the needle is within the housing by sliding the stem toward the second end of the housing and causing the needle to retract through the opening in the first end of the housing;
   c) a means for reversibly locking the stem at a first defined location in said longitudinal slot so as to hold said needle assembly in said first position;
   d) a means for reversibly locking the stem at a second defined location in said longitudinal slot so as to hold said needle assembly in said second position; and
      where the hub of said needle assembly is movably positioned along the defined longitudinal axis of the housing; and
      wherein the housing is manufactured from:
         a first part, comprising a hollow tube having a first end adapted to admit the hollow needle and the second end adapted to admit the needle assembly, said second end having the male joint on its outer surface; and
      the second part, comprising a ring having a female joint adapted to be fitted onto the male joint;
      wherein the longitudinal slot in the housing runs along the length of the hollow tube from the first defined location near the first end of the hollow tube to the second end of the hollow tube, with the longitudinal slot being closed at the second end of the hollow tube and having an opening at the second end of the hollow tube, said opening being adapted to admit the stem on the needle assembly;
      and wherein the longitudinal slot comprises a means for reversibly locking the stem at the first defined location near the first end of the hollow tube, and a means for reversibly locking the stem at the first defined location near the second end of the hollow tube.

20. The retractable needle of claim 19, wherein the ring is fitted onto the joint at the second end of the hollow tube and acts to close the opening in the longitudinal slot.

21. The retractable needle of claim 20, wherein the means for reversibly locking the stem at the first defined location comprises a first pair of teeth on opposite sides of the longitudinal slot, said first pair of teeth being positioned near the first defined location; wherein a locking position is defined between the first pair of teeth and the closed end of the longitudinal slot; and wherein the first pair of teeth cause the width of the longitudinal slot to narrow to a width which is smaller than the diameter of the stem, but which is large enough to allow a user to push the stem through the first pair of teeth.

22. The retractable needle of claim 21, wherein the means for reversibly locking the stem at the second defined location comprises a second pair of teeth on opposite sides of the longitudinal slot, said second pair of teeth being positioned near the second defined location; wherein a locking position is defined between the second pair of teeth and the ring fitted onto the joint at the second end of the hollow tube; and wherein the second pair of teeth cause the width of the longitudinal slot to narrow to a width which is smaller than the diameter of the stem, but which is large enough to allow a user to push the stem through the second pair of teeth.

23. The apparatus of claim 15, wherein the hub has a diameter which is the same as an inner diameter of the housing.

24. The apparatus of claim 15, wherein the hub has a diameter which is less than an inner diameter of the housing.

25. The apparatus of claim 24, wherein the thumbrest is positioned outside of the housing, and is too wide to pass through the longitudinal slot engaging the stem, and
   wherein the stem connecting the thumbrest to the hub is sufficiently long to allow the hub to be positioned along the longitudinal axis of the housing.

26. A retractable needle, comprising:
   a) a needle assembly comprising:
      a cylindrical hub having an anterior end and a posterior end;
      a hollow needle extending through the hub, said needle having a first end adapted to penetrate a blood vessel projecting from the anterior end of the hub and a second end projecting from the posterior end of the hub; and
      a stem having a defined diameter connected with said hub, said stem having a thumbrest rigidly fixed to the stem at a defined distance from the hub;
   b) a housing with a defined longitudinal axis having a tubular wall with a longitudinal slot which is wider than the diameter of the stem therein, said housing having a first end and a second end, wherein the first end has an opening adapted to allow the first end of the hollow needle to pass therethrough, and the second end has an opening adapted to admit an evacuated blood collection tube, said blood collection tube having an elastomeric seal adapted to be penetrated by the second end of the hollow needle;
      said housing having said needle assembly mounted therein so that the stem is slidably engaged by the longitudinal slot, so that said needle assembly may be moved from a first position where the needle passes through the opening in the first end of the housing and is exposed to a second position where the needle is within the housing by sliding the stem toward the second end of the housing and causing the needle to retract through the opening in the first end of the housing;

c) a means for reversibly locking the stem at a first defined location in said longitudinal slot so as to hold said needle assembly in said first position;

d) a means for reversibly locking the stem at a second defined location in said longitudinal slot so as to hold said needle assembly in said second position; and e) a means for preventing blood from flowing through the needle when the first end of the needle penetrates the blood vessel unless the second end of the needle penetrates the seal on the blood collection tube;

where the hub of said needle assembly is movably positioned along the defined longitudinal axis of the housing.

27. The retractable needle of claim 26, wherein the housing is manufactured from two parts.

28. The retractable needle of claim 27, wherein the housing is manufactured from:

a first part, comprising a hollow tube having a first end adapted to admit the hollow needle and a second end adapted to admit the needle assembly, said second end of the first part having a male joint on its outer surface; and a second part, comprising a ring having a female joint adapted to be fitted onto the male joint;

wherein the longitudinal slot in the housing runs along the length of the hollow tube from a first defined location near the first end of the hollow tube to the second end of the hollow tube, with the longitudinal slot being closed at the first end of the hollow tube and having an opening at the second end of the hollow tube, said opening being adapted to admit the stem on the needle assembly;

and wherein the longitudinal slot comprises the means for reversibly locking the stem at the first defined location near the first end of the hollow tube, and the means for reversibly locking the stem at the second defined location near the second end of the hollow tube.

29. The retractable needle of claim 28, wherein the ring is fitted onto the joint at the second end of the hollow tube and acts to close the opening in the longitudinal slot.

30. The retractable needle of claim 29, wherein the means for reversibly locking the stem at the first defined location comprises a first pair of teeth on opposite sides of the longitudinal slot, said first pair of teeth being positioned near the first defined location; wherein a locking position is defined between the first pair of teeth and the closed end of the longitudinal slot; and wherein the first pair of teeth cause the width of the longitudinal slot to narrow to a width which is smaller than the diameter of the stem, but which is large enough to allow a user to push the stem through the first pair of teeth.

31. The retractable needle of claim 29, wherein the means for reversibly locking the stem at the second defined location comprises a second pair of teeth on opposite sides of the longitudinal slot, said second pair of teeth being positioned near the second defined location; wherein a locking position is defined between the second pair of teeth and the cap fitted onto the joint at the second end of the hollow tube; and wherein the second pair of teeth cause the width of the longitudinal slot to narrow to a width which is smaller than the diameter of the stem, but which is large enough to allow a user to push the stem through the second pair of teeth.

32. The apparatus of claim 26, wherein the hub has a diameter which is the same as an inner diameter of the housing.

33. The apparatus of claim 26, wherein the hub has a diameter which is less than an inner diameter of the housing.

34. The apparatus of claim 33, wherein the thumbrest is positioned outside of the housing, and is too wide to pass through the longitudinal slot engaging the stem, and wherein the stem connecting the thumbrest to the hub is sufficiently long to allow the hub to be positioned along the longitudinal axis of the housing.

35. The apparatus of claim 26, wherein the thumbrest is planar.

36. The apparatus of claim 26, wherein the thumbrest is a ring around the tubular housing.

37. A retractable needle, comprising:

a) a needle assembly comprising:

a cylindrical hub having an anterior end and a posterior end, said posterior end of said hub having a frusto-conical cavity therein, said cavity being adapted to frictionally engage a fitting on a syringe barrel;

a hollow needle extending through the hub and projecting from the anterior end of the hub; and a stem having a defined diameter connected with said hub, said stem having a thumbrest rigidly fixed to the stem at a defined distance from the hub;

b) a housing with a defined longitudinal axis having a tubular wall with a longitudinal slot which is wider than the diameter of the stem therein, said housing having a first end and a second end, wherein the first end has an opening adapted to allow the hollow needle to pass therethrough and the second end has an opening adapted to admit the syringe barrel;

wherein said longitudinal slot has a first closed end near the first end of the housing and a second open end at the second end of the housing;

said housing having said needle assembly mounted therein so that the stem is slidably engaged by the longitudinal slot, so that said needle assembly may be moved from a first position where the needle passes through the opening in the first end of the housing and is exposed to a second position where the needle is within the housing by sliding the stem toward the second end of the housing and causing the needle to retract through the opening in the first end of the housing;

c) a means for closing the second open end of the longitudinal slot;

d) a means for reversibly locking the stem at a first defined location in said longitudinal slot so as to hold said needle assembly in said first position; and e) a means for reversibly locking the stem at a second defined location in said longitudinal slot so as to hold said needle assembly in said second position;

wherein the means for reversibly locking the stem at the first defined location comprises a first pair of teeth on opposite sides of the longitudinal slot, said first pair of teeth being positioned near the first defined location; wherein a locking position is defined between the first pair of teeth and a first closed end of the longitudinal slot; and wherein the first pair of teeth causes the width of the longitudinal slot to narrow to a width which is smaller than the diameter of the stem, but which is large enough to allow a user to push the stem through the first pair of teeth; and wherein the means for reversibly locking the stem at the second defined location comprises a second pair of teeth on opposite sides of the longitudinal slot, said second pair of teeth being positioned near the second defined location; wherein a locking position is defined by the second pair of teeth and the means for closing the second open end of the longitudinal slot; and wherein the second pair of teeth causes the width of the longitudinal slot to narrow to a width which is smaller than the diameter of the stem, but which is large enough to allow a user to push the stem through the second pair of teeth.

38. A retractable needle for use with a catheter, comprising:
  a) a needle assembly comprising:
    a cylindrical hub having an anterior end and a posterior end;
    a hollow needle extending through the hub and projecting from the anterior end of the hub;
    a tubular flash chamber having a first end which is connected in a leakproof fashion with the posterior end of the hub, and a second end; and
    a stem having a defined diameter rigidly connected with said hub, said stem being non-rotatable relative to said hub, wherein said stem has a thumbrest rigidly fixed to the stem at a defined distance from the hub;
    where an interior of the hollow needle is in fluid communication with an interior of said tubular flash chamber;
  b) a housing with a defined longitudinal axis having a tubular wall with a longitudinal slot which is wider than the diameter of the stem therein, said housing having a first end of the housing and a second end, wherein the first end has an opening adapted to allow the hollow needle to pass therethrough and the second end of the housing is closed;
    said housing having said needle assembly mounted therein so that the stem is slidably engaged by the longitudinal slot, so that said needle assembly may be moved from a first position where the needle passes through the opening in the first end of the housing and is exposed to a second position where the needle is within the housing by sliding the stem toward the second end of the housing and causing the needle to retract through the opening in the first end of the housing;
  c) a means for reversibly locking the stem at a first defined location in said longitudinal slot so as to hold said needle assembly in said first position;
    wherein the means for reversibly locking the stem at the first defined location comprises a first transverse slot intersecting the longitudinal slot at the first defined location, and a first pair of teeth on opposite sides of the first transverse slot; wherein a locking position is defined between the first pair of teeth and a closed end of the first transverse slot; and wherein the first pair of teeth are separated by a distance which is smaller than the diameter of the stem, but which is large enough to allow a user to push the stem through the first pair of teeth;
  d) a means for reversibly locking the stem at a second defined location in said longitudinal slot so as to hold said needle assembly in said second position; and
  f) a means for removably fastening a catheter to the first end of the housing;
    wherein the needle is adapted to releasably engage a catheter when the needle assembly is in the first position and the needle is exposed; and
    where the hub of said needle assembly is movably positioned along the defined longitudinal axis of the housing.

39. A retractable needle for use with a catheter, comprising:
  a) a hollow needle;
  b) a cylindrical hub, said hollow needle passing axially through said cylindrical hub;
  c) an adjustable-length tube having a first end and a second end, said tube having a length which may be reversibly altered from a first contracted length to a second extended length;
  d) a flash chamber having a first end which is sealed to the first end of the adjustable-length tube so that an interior of the flash chamber is in fluid communication with an interior of the adjustable-length tube;
  e) a means for securing the cylindrical hub to the second end of the adjustable-length tube so that an interior of the hollow needle is in fluid communication with the interior of the adjustable-length tube;
  f) a tubular sheath disposed around the adjustable-length tube; said tubular sheath having a first end which is rigidly connected with both the first end of the adjustable length tube and the flash chamber, and a second end having an opening adapted to allow the hollow needle to pass therethrough; and
  g) a means for reversibly altering the length of the adjustable-length tube from the first contracted length to the second extended length;
    where the needle is entirely disposed within the sheath when the adjustable-length tube is contracted, and where the needle is exposed through the opening in the second end of the sheath when the adjustable-length tube is extended; and
    where the hollow needle is adapted to engage a cannula of a catheter when the needle is exposed.

40. The apparatus of claim 39, wherein the means for reversibly altering the length of the adjustable-length tube comprises a knob having a defined diameter which is connected with the hub, and a longitudinal slot in the tubular sheath, where the longitudinal slot is wider than the diameter of the knob, and the knob is slidably engaged by the longitudinal slot;
  a means for reversibly locking the knob at a first defined location which causes the needle to be exposed; and
  a means for reversibly locking the knob at a second defined location which causes the needle to be disposed within the sheath.

41. The apparatus of claim 40, wherein the means for reversibly locking the knob at the first defined location comprises a first pair of teeth on opposite sides of the longitudinal slot, said first pair of teeth being positioned near the first defined location; wherein a locking position is defined between the first pair of teeth and a first closed end of the longitudinal slot; and wherein the first pair of teeth causes the width of the longitudinal slot to narrow to a width which is smaller than the diameter of the stem, but which is large enough to allow a user to push the stem through the first pair of teeth; and
  wherein the means for reversibly locking the stem at the second defined location comprises a second pair of teeth on opposite sides of the longitudinal slot, said second pair of teeth being positioned near the second defined location; wherein a locking position is defined by the second pair of teeth and a means for closing a second end of the longitudinal slot; and wherein the second pair of teeth causes the width of the longitudinal slot to narrow to a width which is smaller than the diameter of the stem, but which is large enough to allow a user to push the stem through the second pair of teeth.

42. A retractable syringe needle, comprising:

a) a hollow hypodermic needle;

b) a cylindrical hub, said hollow needle passing axially through said cylindrical hub;

c) an adjustable-length tube having a first end and a second end, said tube having a length which may be reversibly altered from a first contracted length to a second extended length;

d) a means for reversibly securing a syringe barrel having a frusto-conical fitting thereon to the first end of the adjustable-length tube so that an interior of the syringe barrel is in fluid communication with an interior of the adjustable-length tube;

e) a means for securing the cylindrical hub to the second end of the adjustable-length tube so that an interior of the hollow needle is in fluid communication with the interior of the adjustable-length tube;

f) a tubular sheath disposed around the adjustable-length tube; said tubular sheath having a first end which is rigidly connected with the first end of the adjustable length tube, and a second end having an opening adapted to allow the hollow hypodermic needle to pass therethrough; and g) a means for reversibly altering the length of the adjustable-length tube from the first contracted length to the second extended length;

wherein the hypodermic needle is entirely disposed within the sheath when the adjustable-length tube is contracted, and where the hypodermic needle is exposed through the opening in the second end of the sheath when the adjustable-length tube is extended;

wherein the means for reversibly altering the length of the adjustable-length tube comprises:

a knob having a defined diameter which is connected with the hub, and a longitudinal slot in the tubular sheath, where the longitudinal slot is wider than the diameter of the knob, and the knob is slidably engaged by the longitudinal slot;

a means for reversibly locking the knob at a first defined location which causes the needle to be exposed; and a means for reversibly locking the knob at a second defined location which causes the needle to be disposed within the sheath;

wherein the means for reversibly locking the knob at the first defined location comprises a first pair of teeth on opposite sides of the longitudinal slot, said first pair of teeth being positioned near the first defined location; wherein a locking position is defined between the first pair of teeth and a first closed end of the longitudinal slot; and wherein the first pair of teeth causes the width of the longitudinal slot to narrow to a width which is smaller than the diameter of the stem, but which is large enough to allow a user to push the stem through the first pair of teeth; and wherein the means for reversibly locking the stem at the second defined location comprises a second pair of teeth on opposite sides of the longitudinal slot, said second pair of teeth being positioned near the second defined location; wherein a locking position is defined by the second pair of teeth and a means for closing a second end of the longitudinal slot; and wherein the second pair of teeth causes the width of the longitudinal slot to narrow to a width which is smaller than the diameter of the stem, but which is large enough to allow a user to push the stem through the second pair of teeth.

\* \* \* \* \*